United States Patent
Amberg et al.

[11] Patent Number: 6,004,988
[45] Date of Patent: Dec. 21, 1999

[54] CARBOXYLIC ACID DERIVATIVES, THEIR PREPARATION AND THEIR USE

[75] Inventors: Wilhelm Amberg, Friedrichsdorf; Andreas Kling, Mannheim; Dagmar Klinge, Heidelberg; Hartmut Riechers, Neustadt; Liliane Unger, Ludwigshafen; Manfred Raschack, Weisenheim; Stefan Hergenröder, Mainz; Bernd Elger, Neustadt; Sabine Schult, Speyer, all of Germany

[73] Assignee: BASF Aktiengesellschaft, Ludwigshafen, Germany

[21] Appl. No.: 09/029,447
[22] PCT Filed: Aug. 29, 1996
[86] PCT No.: PCT/EP96/03793
§ 371 Date: Feb. 24, 1998
§ 102(e) Date: Feb. 24, 1998
[87] PCT Pub. No.: WO97/09294
PCT Pub. Date: Mar. 13, 1997

[30] Foreign Application Priority Data

Sep. 7, 1995 [DE] Germany .............................. 195 33 025

[51] Int. Cl.⁶ .................. A61K 31/19; A61K 31/275; A61K 31/41; C07C 59/64; C07D 257/04
[52] U.S. Cl. .................. 514/381; 514/277; 514/311; 514/314; 514/356; 514/363; 514/365; 514/372; 514/374; 514/378; 514/382; 514/415; 514/438; 514/443; 514/452; 514/456; 514/461; 514/464; 514/466; 514/468; 514/469; 514/471; 514/520; 514/569; 514/570; 514/335; 546/174; 546/342; 548/136; 548/204

[58] Field of Search ................... 562/466, 468, 562/490, 491; 558/388, 408, 410; 548/250, 252, 254; 549/365, 447; 514/381, 382, 452, 464, 520, 569, 570

[56] References Cited

FOREIGN PATENT DOCUMENTS

95/03295  2/1995  WIPO.
94/2747   3/1995  WIPO.

OTHER PUBLICATIONS

Tanaka et al., Chem. Pharm. Gull., vol. 26, pp. 1558–1569, 1978.

*Primary Examiner*—Richard L. Raymond
*Attorney, Agent, or Firm*—Keil & Weinkauf

[57] ABSTRACT

Carboxylic acid derivatives of the formula I

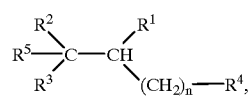

(I)

here $R^1$ is a tetrazole [sic], nitrile [sic], a group COOH or a radical which can be hydrolyzed to COOH, and the other substituents have the meaning explained in the description.

3 Claims, No Drawings

CARBOXYLIC ACID DERIVATIVES, THEIR PREPARATION AND THEIR USE

This application is a 371 or PCT/EP96/03793, filed Aug. 29, 1996.

The present invention relates to novel carboxylic acid derivatives, their preparation and use.

Endothelin is a peptide which is composed of 21 amino acids and is synthesized and released by the vascular endothelium. Endothelin exists in three isoforms, ET-1, ET-2 and ET-3. Endothelin or ET hereinafter indicates one or all isoforms of endothelin. Endothelin is a potent vasoconstrictor and has a great effect on vascular tone. It is known that this vasoconstriction is caused by the binding of endothelin to its receptor (Nature, 332, 411–415, 1988; FEBS Letters, 231, 440–444, 1988 and Biochem. Biophys. Res. Commun., 154, 868–875, 1988).

Increased or abnormal release of endothelin causes persistent vasoconstriction in peripheral, renal and cerebral blood vessels, which may lead to diseases. As reported in the literature, elevated levels of endothelin in plasma have been found in patients with hypertension, acute myocardial infarct, pulmonary hypertension, Raynaud's syndrome, atherosclerosis and in the airways of asthmatics (Japan J. Hypertension, 12, 79 (1989), J. Vascular Med. Biology 2, 207 (1990), J. Am. Med. Association 264, 2868 (1990)).

Accordingly, substances which specifically inhibit the binding of endothelin to the receptor should also antagonize the various abovementioned physiological effects of endothelin and therefore be valuable drugs.

It has been found (WO 94/02474) that certain carboxylic acid derivatives with the general formula Q are good inhibitors of endothelin receptors

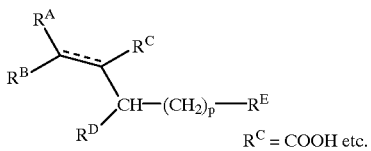

$R^C$ = COOH etc.

However, this related mainly to compounds with a double bond in the molecule. Besides $R^A$ and $R^B$, a maximum of one hydrogen atom is permitted on the β center.

It has now been found, surprisingly, that this hydrogen atom can be replaced by alkyl radicals. This results in a quaternary β center with, at the same time, a large increase in the activity with regard to endothelin receptors (see Examples).

The invention relates to carboxylic acid derivatives of the formula I

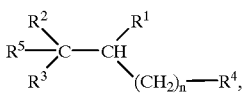

where $R^1$ is a tetrazole [sic], nitrile [sic], COOH or a radical which can be hydrolyzed to COOH, and the other substituents have the following meanings:

$R^2$ and $R^3$ (which can be identical or different):
  phenyl or naphthyl which can be substituted by one or more of the following radicals: halogen, cyano, $NO_2$, hydroxyl, $C_1-C_4$-alkyl, $C_1-C_4$-haloalkyl, $C_1-C_4$-alkoxy, $C_1-C_4$-haloalkoxy, phenoxy, $C_1-C_4$-alkylthio, amino, benzyloxy, $C_1-C_4$-alkylamino or $C_1-C_4$-dialkylamino; or
  phenyl or naphthyl which are connected together in the ortho positions by a direct linkage, a methylene, ethylene or ethenylene group, or an oxygen or sulfur atom;

$R^4$ phenyl or naphthyl, methylenedioxyphenyl, ethylenedioxyphenyl, indanyl, indolyl, pyridyl, benzopyranyl, furanyl, benzofuranyl, isooxazolyl, isothiazolyl, 1,3,4-thiadiazolyl, pyrimidinyl, 2,3-dihydrobenzofuranyl, benzothienyl, quinolinyl, $C_3-C_7$-cycloalkyl, thienyl, oxazolyl, thiazolyl, each of which can be substituted by one or more of the following radicals: halogen, cyano, hydroxyl, $NO_2$, $C_1-C_4$-alkyl, $C_1-C_4$-haloalkyl, $C_1-C_4$-alkoxy, $C_1-C_4$-haloalkoxy, phenoxy, $C_1-C_4$-alkylthio, amino, benzyloxy, $C_1-C_4$-alkylamino or $C_1-C_4$-dialkylamino, it being possible for the alkyl radicals together to form a ring;

$R^5$ $C_1-C_8$-alkyl, $C_3-C_6$-alkenyl, $C_3-C_6$-alkynyl or $C_3-C_8$-cycloalkyl, it being possible for each of these radicals to be substituted one or more times by: halogen, $C_1-C_4$-alkoxy, $C_1-C_4$-alkylthio, $C_1-C_4$-alkylamino, di-$C_1-C_4$-alkylamino;
  phenyl, benzyl, 1-methylnaphthyl, 2-methylnaphthyl or naphthyl, each of which can be substituted by one or more of the following radicals: halogen, cyano, hydroxyl, amino, $C_1-C_4$-alkyl, $C_1-C_4$-alkoxy, phenoxy, $C_1-C_4$-alkylthio, dioxomethylene [sic] or dioxoethylene [sic];

n 1–2.

The compounds, and the intermediates for preparing them, such as Va, may have one or more asymmetric substituted carbon atoms. Compounds of this type may be in the form of pure enantiomers or pure diastereomers or of a mixture thereof. The use of an enantiomerically pure compound as agent is preferred.

The invention furthermore relates to the use of the abovementioned carboxylic acid derivatives for producing drugs, in particular for producing inhibitors of endothelin receptors.

Compounds of the formula I can be prepared by initially reacting a ketone of type II with a phosphono ester of the formula III in the presence of a base to give compounds of the formula IV

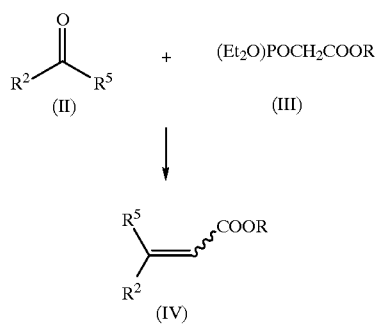

Aprotic polar solvents such as DMF or TRF are used as solvent.

It is possible to use as base an alkali metal or alkaline earth metal hydride such as sodium hydride, potassium hydride or calcium hydride, a carbonate such as alkali metal carbonate, eg. sodium or potassium carbonate, an alkali metal or alkaline earth metal hydroxide such as sodium or potassium hydroxide, an organometallic compound such as butyllithium, an alkali metal alcoholate such as sodium ethanolate or potassium tert-butanolate or an alkali metal amide such as lithium diisopropylamide.

The reaction is preferably carried out at a temperature in the range from 0° C. to the boiling point of the solvent or solvent mixture.

The compounds of type IV can then be reacted with aromatic compounds in the presence of a catalyst to give carboxylic acid derivatives of the general formula Va

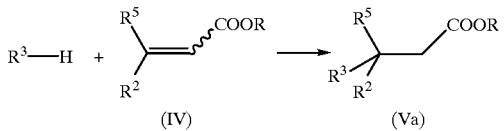

Suitable catalysts for this are strong inorganic acids and Lewis acids. Examples thereof are, inter alia, sulfuric acid, aluminum trichloride, zinc chloride or iron trichloride. When sulfuric acid is used, the free acid can be obtained directly.

Alternatively, symmetrical carboxylic acid derivatives of the formula Vb can be prepared from a β-dicarbonyl compound VI and an aromatic compound in the presence of a catalyst.

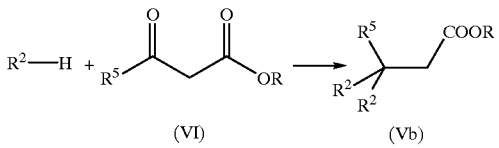

Suitable catalysts for this are strong inorganic acids and Lewis acids. Examples thereof are, inter alia, sulfuric acid, aluminum trichloride, zinc chloride or iron trichloride (see also: Gogte G. R. et al., J. Univ. Bombay, Sect. A, 27, 1958, 41).

Another possibility for preparing compounds of type Va can start from a ketone VII

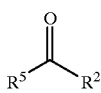

(VII)

which can be reacted with Meldrum's acid in the presence of a base such as pyridine or sodium hydride to give compounds of type VIII (VIII)

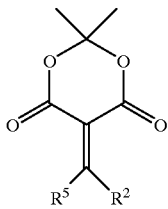

Reaction of compounds of type VIII in diethyl ether with a Grignard reagent of the general formula IX $R^3$—Mg Y (IX)

Y=Br, Cl, I (IX)

results in compounds of type X (X)

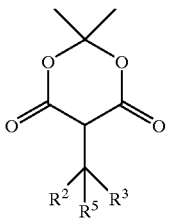

in which case it may be advantageous to use in addition copper salts such as copper chloride, copper bromide, copper iodide or copper cyanide and for a Lewis acid such as trimethylsilyl chloride or boron trifluoride etherate to be present.

Hydrolysis of compounds of the formula X with mineral acids such as hydrochloric acid or sulfuric acid can then afford the compounds Va (R=OH).

Further possibilities for preparing compounds Va are similar to the methods of Zimmermann H. E. et al. J. Am. Chem, Soc. 83 (1961) 1196 or Yu A.J. et al. J. Org. Chem. 23 (1958) 1004.

Compounds of the formula Va,b can be converted into the anion (or dianion for R=H) with a strong base such as butyllithium or lithium diisopropylamide in an inert solvent such as diethyl ether or tetrahydrofuran and under inert gas, eg. nitrogen or argon, at −78° C. to room temperature. This anion reacts with alkylating agents of type VII at −78° C. to room temperature.

Quenching with concentrated $NH_4Cl$ or dilute mineral acid such as HCl results in compounds of the formula I

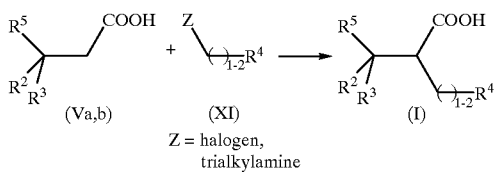

Z = halogen, trialkylamine

Compounds of type I with $R^1$=tetrazole [sic] can be synthesized starting from the carboxylic acids I ($R^1$=COOH). To do this, the carboxylic acid is reacted with thionyl chloride at room temperature to give the acid chloride, which is then reacted with aqueous ammonia solution to give the amide of the formula XII.

(XII)

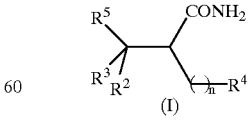

Amides of the formula XII can be reacted with oxalyl chloride or phosphorus oxychloride or trifluoroacetic anhydride in DMF or pyridine at 0° C. to room temperature to give nitriles of the formula XIII

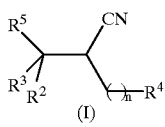

(I)

Reaction of nitriles of the formula XIII with sodium azide or trimethylsilyl azide in a suitable solvent such as dimethylformamide, tetrahydrofuran or 1-methyl-2-pyrrolidinone in the presence of a catalyst such as ammonium chloride (see also: Bernsteim P. R. et al., Synthesis, 1987, 1133) at room temperature or elevated temperature affords the tetrazoles XIV

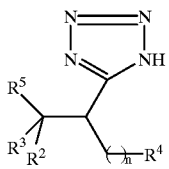

(XIV)

Compounds of the formula I can also be prepared by starting from the corresponding carboxylic acids, ie. compounds of the formula I where $R^1$=COOH, and converting these initially in a conventional way into an activated form such as an acid halide, an anhydride or imidazolide, and then reacting the latter with an appropriate hydroxyl compound HOR. This reaction can be carried out in conventional solvents and often requires the addition of a base, in which case those mentioned above are suitable. These two steps can also be simplified, for example, by allowing the carboxylic acid to act on the hydroxyl compound in the presence of a dehydrating agent such as a carbodiimide.

Compounds of the formula I can also be prepared by starting from salts of the corresponding carboxylic acids, ie. from compounds of the formula I where $R^1$ is COR and R is OM, where M can be an alkali metal cation or the equivalent of an alkaline earth metal cation. These salts can be reacted with many compounds of the formula R-A where A is a conventional nucleofugic leaving group, for example halogen such as chlorine, bromine, iodine, or aryl- or alkylsulfonyl which is unsubstituted or substituted by halogen, alkyl or haloalkyl, such as toluenesulfonyl and methylsulfonyl, or another equivalent leaving group. Compounds of the formula R-A with a reactive substituent A are known or can easily be obtained with general expert knowledge. This reaction can be carried out in the usual solvents and is advantageously carried out with the addition of a base, in which case those mentioned above are suitable.

Enantiomerically pure compounds of the formula I can be obtained by carrying out with racemic or diastereomeric compounds of the formula VI a classical racemate resolution with suitable enantiomerically pure bases such as brucine, strychnine, quinine, quinidine, cinchonidine, cinchonine, yohimbine, morphine, dehydroabietylamine, ephedrine (−), (+), deoxyephedrine (−) (+) threo-2-amino-1-(p-nitrophenyl)-1,3-propanediol (−) , (+), threo-2-(N,N-dimethylamino)-1-(p-nitrophenyl)-1,3-propanediol (+), (−) threo-2-amino-1-phenyl-1,3-propanediol (+), (−) α-methylbenzylamine (+), (−) , α-(1-naphthyl)ethylamine (+), (−) α-(2-naphthyl)ethylamine (+), (−) , aminomethylpinane, N,N-dimethyl-1-phenylethylamine, N-methyl-1-phenylethylamine, 4-nitrophenylethylamine, pseudoephedrine, norephedrine, norpseudoephedrine, amino acid derivatives and peptide derivatives.

Wide variation is possible in the radical $R^1$ in formula I. For example, $R^1$ is a group

where R has the following meanings:
a) a succinylimidoxy [sic] group;
b) a 5-membered heteroaromatic radical which is linked via a nitrogen atom, such as pyrrolyl, pyrazolyl, imidazolyl and triazolyl, and which can carry one or two halogen atoms, especially fluorine and chlorine, and/or one or two of the following radicals:

$C_1$–$C_4$-alkyl such as methyl, ethyl, 1-propyl, 2-propyl, 2-methyl-2-propyl, 2-methyl-1-propyl, 1-butyl, 2-butyl;

$C_1$–$C_4$-haloalkyl, especially $C_1$–$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$–$C_4$-haloalkoxy, especially $C_1$–$C_2$-haloalkoxy such as difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 252,2-trifluoroethoxy, 2-chloro-1, 1,2-trifluoroethoxy and pentafluoroethoxy, especially trifluoromethoxy;

$C_1$–$C_4$-alkoxy such as methoxy, ethoxy, propoxy, 1-methylethoxy, butoxy, 1-methylpropoxy, 2-methylpropoxy, 1,1-dimethylethoxy, especially methoxy, ethoxy, 1-methylethoxy;

$C_1$–$C_4$-alkylthio such as methylthio, ethylthio, propylthio, 1-methylethylthio, butylthio, 1-methylpropylthio, 2-methylpropylthio, 1,1-dimethylethylthio, especially methylthio and ethylthio;

c) R furthermore a radical

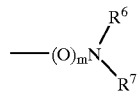

where m is 0 or 1 and $R^6$ and $R^7$, which can be identical or different, have the following meanings:
hydrogen
$C_1C_8$-alkyl, especially $C_1$–$C_4$-alkyl as mentioned above;
$C_3$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2- dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, especially 2-propenyl, 2-butenyl, 3-methyl-2-butenyl and 3-methyl-2-pentenyl;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, especially 2-propynyl $C_3$–$C_8$-cycloalkyl, such as cyclopropyl, cyclobutyl, cyclopentyl, cyclohexyl and cycloheptyl, cyclooctyl, it being possible for these alkyl, cycloalkyl, alkenyl and alkynyl groups each to carry one to five halogen atoms, especially fluorine or chlorine, and/or one or two of the following groups:

$C_1$–$C_4$-alkyl, $C_1$–$C_4$-alkoxy, $C_1$–$C_4$-alkylthio, $C_1$–$C_4$-haloalkoxy as mentioned above, $C_3$–$C_6$-alkenyloxy, $C_3$–$C_6$-alkenylthio, $C_3$–$C_6$-alkynyloxy, $C_3$–$C_6$-alkynylthio, with the alkenyl and alkynyl constituents in these radicals preferably corresponding to the abovementioned meanings;

$C_1$–$C_4$-alkylcarbonyl such as, in particular, methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$–$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl;

$C_3$–$C_6$-alkenylcarbonyl, $C_3$–$C_6$-alkynylcarbonyl, $C_3$–$C_6$-alkenyloxycarbonyl and $C_3$–$C_6$-alkynyloxycarbonyl, where the alkenyl and alkynyl radicals are preferably defined as specifically stated above;

phenyl, unsubstituted or mono- or polysubstituted, eg. mono- to trisubstituted, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, such as 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl;

di-$C_1$–$C_4$-alkylamino such as, in particular, dimethylamino, dipropylamino, N-propyl-N-methylamino, N-propyl-N-ethylamino, diisopropylamino, N-Isopropyl-N-methylamino, N-isopropyl-N-ethylamino, N-Isopropyl-N-propylamino;

$R^6$ and $R^7$ furthermore phenyl which can be substituted by one or more, eg. one to three, of the following radicals: halogen, nitro, cyano, $C_1$–$C_4$-Alkyl, $C_1$–$C_4$-haloalkyl, $C_1$–$C_4$-alkoxy, $C_1$–$C_4$-haloalkoxy or $C_1$–$C_4$-alkylthio, as mentioned above in particular;

or $R^6$ and $R^7$ together form a $C_4$–$C_7$-alkylene chain which is closed to form a ring, is unsubstituted or substituted, eg. by $C_1$–$C_4$-alkyl, and which may contain a heteroatom selected from the group of oxygen, sulfur or nitrogen, such as —(CH$_2$)$_4$—, —(CH$_2$)$_5$—, —(CH$_2$)$_6$—, —(CH$_2$)$_7$—, —(CH$_2$)$_2$—O—)CH$_2$)$_2$—, —CH$_2$—S—(CH$_2$)$_3$—, —(CH$_2$)$_2$—O—(CH$_2$)$_3$—, —NH—(CH$_2$)$_3$—, —CH$_2$—NH—(CH$_2$)$_2$—, —CH$_2$—CH=CH—CH$_2$—, —CH=CH—(CH$_2$) 3—;

d) R furthermore a group

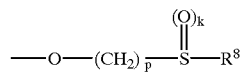

where k is 0, 1 and 2, p is 1, 2, 3 and 4, and $R^8$ is
$C_1$–$C_4$-alkyl, $C_1$–$C_4$-haloalkyl, $C_3$–$C_6$-alkenyl, $C_3$–$C_6$-alkynyl or unsubstituted or substituted phenyl, such as mentioned above in particular.

e) R furthermore a radical $OR^9$ where $R^9$ is:
hydrogen, the cation of an alkali metal such as lithium, sodium, potassium or the cation of an alkaline earth metal such as calcium, magnesium and barium, or an environmentally compatible organic ammonium ion such as tertiary $C_1$–$C_4$-alkylammonium or the ammonium ion;

$C_3$–$C_8$-cycloalkyl as mentioned above, which can carry one to three $C_1$–$C_4$-alkyl groups;

$C_1$–$C_8$-alkyl such as, in particular, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which can carry one to five halogen atoms, in particular fluorine and chlorine, and/or one of the following radicals:

$C_1$–$C_4$-alkoxy, $C_1$–$C_4$-alkylthio, cyano, $C_1$–$C_4$-alkylcarbonyl, $C_3$–$C_8$-cycloakyl, $C_1$1 $C_4$-alkoxycarbonyl, phenyl, phenoxy or phenylcarbonyl, where the aromatic radicals in turn can each carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, as mentioned above in particular;

$C_1$–$C_8$-alkyl as mentioned above, which can carry one to five halogen atoms, in particular fluorine and/or chlorine, and carries one of the following radicals: a 5-membered heteroaromatic radical containing one to three nitrogen atoms, or a 5-membered heteroaromatic radical containing one nitrogen atom and one oxygen or sulfur atom, which can carry one to four halogen atoms and/or one or two of the following radicals:

nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropyl-5-isoxazolyl, 3-methyl-5-isoxazolyl, 2-oxazolyl, 2-thiazolyl, 2-imidazolyl, 3-ethyl-5-isoxazolyl, 3-phenyl-5-isoxazolyl, 3-tert-butyl-5-isoxazolyl;

$C_2$–$C_6$-alkyl which has in position 2 one of the following radicals: $C_1$–$C_4$-alkoxyimino, $C_3$–$C_6$-alkynyloxyimino, $C_3$–$C_6$-haloalkenyloxyimino or benzyloxyimino;

$C_3$–$C_6$-alkenyl or $C_3$–$C_6$-alkynyl, it being possible for these groups in turn to carry one to five halogen atoms;

$R^9$ furthermore a phenyl radical which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, as mentioned above in particular;

a 5-membered heteroaromatic radical which is linked via a nitrogen atom and contains one to three nitrogen atoms and which can carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloro-1-imidazolyl;

$R^9$ furthermore a group

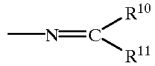

where $R^{10}$ and $R^{11}$, which can be identical or different, are:

$C_1$–CS-alkyl, $C_3$–$C_6$-alkenyl, $C_3$–$C_6$-alkynyl, $C_3$–$C_8$-Cycloalkyl, it being possible for these radicals to carry a $C_1$–$C_4$-alkoxy, $C_1$–$C_4$-alkylthio and/or an unsubstituted or substituted phenyl radical, as mentioned above in particular;

phenyl, which can be substituted by one or more, eg. one to three, of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, where these radicals correspond in particular to those mentioned above;

or $R^{10}$ and $R^{11}$ together form a $C_3$–$C_{12}$-alkylene chain which can carry one to three $C_1$–$C_4$-alkyl groups and contain a heteroatom from the group of oxygen, sulfur and nitrogen, as mentioned in particular for R6 and $R^7$.

f) R furthermore a radical

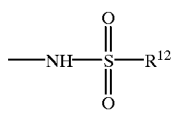

where $R^{12}$ is:
$C_1$–$C_4$-alkyl, $C_3$–$C_6$-alkenyl, $C_3$–$C_6$-alkynyl, $C_3$-$C_8$-cycloalkyl as mentioned above in particular, it being possible for these radicals to carry a $C_1$–$C_4$-alkoxy, $C_1$–$C_4$-alkylthio and/or a phenyl radical as mentioned above;

phenyl, unsubstituted or substituted, in particular as mentioned above.

g) R a radical

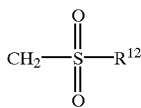

where $R^{12}$ has the abovementioned meanings.

$R^1$ can furthermore be:
tetrazole [sic] or nitrile [sic].

With a view to the biological effect, preferred carboxylic acid derivatives of the general formula I, both as pure enantiomers and pure diastereomers and as mixtures thereof, are those where the substituents have the following meanings:

$R^1$ tetrazole [sic], COOH or a radical which can be hydrolyzed to COOH;

$R^2$ and $R^3$ (which can be identical or different);

phenyl or naphthyl which can be substituted by one or more of the following radicals: F, Cl, Br, I, cyano, $NO_2$, hydroxyl, methyl, ethyl, propyl, isopropyl, trifluoromethyl, 2,2,2-trifluoroethyl, methoxy, ethoxy, propoxy, isopropoxy, trifluoromethyloxy, phenoxy, methylthio, ethylthio, benzyloxy, amino, methylamino, dimethylamino;

$R^4$ phenyl, methylenedioxyphenyl, ethylenedioxyphenyl, indanyl, pyridyl, 2,3-dihydrobenzofuranyl, benzofuranyl, benzothienyl, 2-pyrimidinyl, 4-pyrimidinyl, 2,3-dihydrobenzothienyl, each of which can be substituted by one or more of the following radicals: F, Cl, Br, I, cyano, $NO_2$, methyl, ethyl, propyl, isopropyl, trifluoromethyl, methoxy, ethoxy, propoxy, isopropoxy, butyloxy, tert-butyloxy, trifluoromethyloxy, phenoxy, methylthio, ethylthio, propylthio, benzyloxy, amino, methylamino, dimethylamino;

$R^5$ methyl, ethyl, propyl, isopropyl, butyl, 2-methylpropyl, tert-butyl, pentyl, 3-methylbutyl, hexyl, 3-pentyl, 4-methylpentyl, 2-ethylbutyl, each of which can be substituted one or more times by: cyano, methoxy, ethoxy, propoxy, isopropoxy, butoxy, methylthio, ethylthio, propylthio, isopropylthio, amino, methylamino, dimethylamino;

allyl, vinyl, trifluoromethyl, 2,2,2-trifluoroethyl;

phenyl, benzyl, each of which can be substituted by one or is more of the following radicals: F, Cl, Br, I, hydroxyl, methyl, ethyl, propyl, isopropyl, methoxy, ethoxy, propoxy, isopropoxy, methylthio, ethylthio, dioxomethylene [sic], dioxoethylene [sic];

n 1–2

Examples of preferred compounds are listed in the following Table:

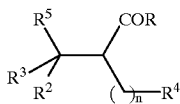

| No. | R | R² | R³ | R⁵ | R⁴ | n |
|---|---|---|---|---|---|---|
| 1 | OH | Phenyl | Phenyl | Methyl | Phenyl | 1 |
| 2 | OH | Phenyl | Phenyl | Methyl | 3,5-Dimethylphenyl | 1 |
| 3 | OH | Phenyl | Phenyl | Methyl | 3,5-Dimethoxyphenyl | 1 |
| 4 | OH | Phenyl | Phenyl | Methyl | 3,4-Methylenedioxyphenyl | 1 |
| 5 | OH | Phenyl | Phenyl | Methyl | 2,3-Dihydro-benzofuran-5-yl | 1 |
| 6 | OH | Phenyl | Phenyl | Methyl | 2,3-Dihydro-1H-inden-5-yl | 1 |
| 7 | OH | Phenyl | Phenyl | Methyl | 3-Methoxy-5-methylphenyl | 1 |
| 8 | OH | Phenyl | Phenyl | Methyl | 3,4-Ethylenedioxyphenyl | 1 |
| 9 | OH | Phenyl | Phenyl | Methyl | 5-Methoxy-3,4-methylenedioxyphenyl | 1 |
| 10 | OH | Phenyl | Phenyl | Methyl | 3,5-Diethylphenyl | 1 |
| 11 | OH | Phenyl | Phenyl | Methyl | 3,4-Dimethoxyphenyl | 1 |
| 12 | OH | Phenyl | Phenyl | Methyl | 3-Methyl-4-benzyloxyphenyl | 1 |
| 13 | OH | Phenyl | Phenyl | Methyl | 3-Benzyloxy-5-methoxyphenyl | 1 |
| 14 | OH | Phenyl | Phenyl | Methyl | 3-Benzyloxy-4-methoxyphenyl | 1 |
| 15 | OH | Phenyl | Phenyl | Methyl | 3-Hydroxy-4-methoxyphenyl | 1 |
| 16 | OH | Phenyl | Phenyl | Methyl | 4-Hydroxy-3-methoxyphenyl | 1 |
| 17 | OH | Phenyl | Phenyl | Methyl | 3,5-Bis-(trifluoromethyl)-phenyl | 1 |
| 18 | OH | Phenyl | Phenyl | Methyl | 3-Methylphenyl | 1 |
| 19 | OH | Phenyl | Phenyl | Methyl | 3-Methoxyphenyl | 1 |
| 20 | OH | Phenyl | Phenyl | Methyl | 4-Benzyloxyphenyl | 1 |
| 21 | OH | Phenyl | Phenyl | Methyl | 4-Phenoxyphenyl | |
| 22 | OH | Phenyl | Phenyl | Methyl | 6-Methylpyridin-2-yl | 1 |
| 23 | OH | Phenyl | Phenyl | Methyl | 6-Ethylpyridin-2-yl | 1 |
| 24 | OH | Phenyl | Phenyl | Methyl | 6-Methoxypyridin-2-yl | 1 |
| 25 | OH | Phenyl | Phenyl | Methyl | 4,6-Dimethylpyridin-2-yl | 1 |
| 26 | OH | Phenyl | Phenyl | Methyl | 4,6-Diethylpyridin-2-yl | 1 |
| 27 | OH | Phenyl | Phenyl | Methyl | 4-Methyl-6-methoxypyridin-2-yl | 1 |
| 28 | OH | Phenyl | Phenyl | Methyl | 6,7-Dihydro-5H-cyclopenta[b]pyridin-2-yl | 1 |
| 29 | OH | Phenyl | Phenyl | Methyl | 4,6-Dimethylpyrimidin-2-yl | 1 |
| 30 | OH | Phenyl | Phenyl | Methyl | 4-Methoxy-6-methylpyrimidin-2-yl | 1 |
| 31 | OH | Phenyl | Phenyl | Methyl | 4,6-Dimethoxypyrimidin-2-yl | 1 |
| 32 | OH | Phenyl | Phenyl | Methyl | 4,6-Diethylpyrimidin-2-yl | 1 |
| 33 | OH | Phenyl | Phenyl | Methyl | 6,7-Dihydro-5H-cyclopentapyrimidin-2-yl | 1 |
| 34 | OH | Phenyl | Phenyl | Methyl | Naphth-2-yl | |
| 35 | OH | Phenyl | Phenyl | Methyl | 6,7-Dihydro-5H-cyclopenta[c]pyridin-2-yl | 1 |
| 36 | OH | p-Methoxyphenyl | p-Methoxyphenyl | Methyl | Phenyl | 1 |
| 37 | OH | p-Methoxyphenyl | p-Methoxyphenyl | Methyl | 3,5-Dimethylphenyl | 1 |
| 38 | OH | p-Methoxyphenyl | p-Methoxyphenyl | Methyl | 3,5-Dimethoxyphenyl | 1 |
| 39 | OH | p-Methoxyphenyl | p-Methoxyphenyl | Methyl | 3,4-Methylenedioxyphenyl | 1 |
| 40 | OH | p-Methoxyphenyl | p-Methoxyphenyl | Methyl | 2,3-Dihydro-benzofuran-5-yl | 1 |
| 41 | OH | p-Methoxyphenyl | p-Methoxyphenyl | Methyl | 2,3-Dihydro-1H-inden-5-yl | 1 |
| 42 | OH | p-Methoxyphenyl | p-Methoxyphenyl | Methyl | 3-Methoxy-5-methylphenyl | 1 |
| 43 | OH | p-Methoxyphenyl | p-Methoxyphenyl | Methyl | 3,4-Ethylenedioxyphenyl | 1 |
| 44 | OH | p-Methoxyphenyl | p-Methoxyphenyl | Methyl | 5-Methoxy-3,4-methylenedioxyphenyl | 1 |
| 45 | OH | p-Methoxyphenyl | p-Methoxyphenyl | Methyl | 3,5-Diethylphenyl | 1 |
| 46 | OH | p-Methoxyphenyl | p-Methoxyphenyl | Methyl | 3,4-Dimethoxyphenyl | 1 |
| 47 | OH | p-Methoxyphenyl | p-Methoxyphenyl | Methyl | 3-Methyl-4-benzyloxyphenyl | 1 |
| 48 | OH | p-Methoxyphenyl | p-Methoxyphenyl | Methyl | 3-Benzyloxy-5-methoxyphenyl | 1 |
| 49 | OH | p-Methoxyphenyl | p-Methoxyphenyl | Methyl | 3-Benzyloxy-4-methoxyphenyl | 1 |
| 50 | OH | p-Methoxyphenyl | p-Methoxyphenyl | Methyl | 3-Hydroxy-4-methoxyphenyl | 1 |
| 51 | OH | p-Methoxyphenyl | p-Methoxyphenyl | Methyl | 4-Hydroxy-3-methoxyphenyl | 1 |
| 52 | OH | p-Methoxyphenyl | p-Methoxyphenyl | Methyl | 3,5-Bis-(trifluoromethyl)-phenyl | 1 |
| 53 | OH | p-Methoxyphenyl | p-Methoxyphenyl | Methyl | 3-Methylphenyl | 1 |
| 54 | OH | p-Methoxyphenyl | p-Methoxyphenyl | Methyl | 3-Methoxyphenyl | 1 |
| 55 | OH | p-Methoxyphenyl | p-Methoxyphenyl | Methyl | 4-Benzyloxyphenyl | 1 |
| 56 | OH | p-Methoxyphenyl | p-Methoxyphenyl | Methyl | 4-Phenoxyphenyl | 1 |
| 57 | OH | p-Methoxyphenyl | p-Methoxyphenyl | Methyl | 6-Methylpyridin-2-yl | 1 |
| 58 | OH | p-Methoxyphenyl | p-Methoxyphenyl | Methyl | 6-Ethylpyridin-2-yl | 1 |
| 59 | OH | p-Methoxyphenyl | p-Methoxyphenyl | Methyl | 6-Methoxypyridin-2-yl | 1 |
| 60 | OH | p-Methoxyphenyl | p-Methoxyphenyl | Methyl | 4,6-Dimethylpyridin-2-yl | 1 |
| 61 | OH | p-Methoxyphenyl | p-Methoxyphenyl | Methyl | 4,6-Diethylpyridin-2-yl | 1 |
| 62 | OH | p-Methoxyphenyl | p-Methoxyphenyl | Methyl | 4-Methyl-6-methoxypyridin-2-yl | 1 |
| 63 | OH | p-Methoxyphenyl | p-Methoxyphenyl | Methyl | 6,7-Dihydro-5H-cyclopenta[b]pyridin-2-yl | 1 |
| 64 | OH | p-Methoxyphenyl | p-Methoxyphenyl | Methyl | 4,6-Dimethylpyrimidin-2-yl | 1 |
| 65 | OH | p-Methoxyphenyl | p-Methoxyphenyl | Methyl | 4-Methoxy-6-methylpyrimidin-2-yl | 1 |
| 66 | OH | p-Methoxyphenyl | p-Methoxyphenyl | Methyl | 4,6-Dimethoxypyrimidin-2-yl | 1 |
| 67 | OH | p-Methoxyphenyl | p-Methoxyphenyl | Methyl | 4,6-Diethylpyrimidin-2-yl | 1 |
| 68 | OH | p-Methoxyphenyl | p-Methoxyphenyl | Methyl | 6,7-Dihydro-5H-cyclopentapyrimidin-2-yl | 1 |
| 69 | OH | p-Methoxyphenyl | p-Methoxyphenyl | Methyl | Naphth-2-yl | |
| 70 | OH | p-Methoxyphenyl | p-Methoxyphenyl | Methyl | 6,7-Dihydro-5H-cyclopenta[c]pyridin-2-yl | 1 |
| 71 | OH | p-Methylphenyl | p-Methylphenyl | Methyl | Phenyl | 1 |

-continued

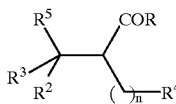

| No. | R | R² | R³ | R⁵ | R⁴ | n |
|---|---|---|---|---|---|---|
| 72 | OH | p-Methylphenyl | p-Methylphenyl | Methyl | 3,5-Dimethylphenyl | 1 |
| 73 | OH | p-Methylphenyl | p-Methylphenyl | Methyl | 3,5-Dimethoxyphenyl | 1 |
| 74 | OH | p-Methylphenyl | p-Methylphenyl | Methyl | 3,4-Methylenedioxyphenyl | 1 |
| 75 | OH | p-Methylphenyl | p-Methylphenyl | Methyl | 2,3-Dihydro-benzofuran-5-yl | 1 |
| 76 | OH | p-Methylphenyl | p-Methylphenyl | Methyl | 2,3-Dihydro-1H-inden-5-yl | 1 |
| 77 | OH | p-Methylphenyl | p-Methylphenyl | Methyl | 3-Methoxy-5-methylphenyl | 1 |
| 78 | OH | p-Methylphenyl | p-Methylphenyl | Methyl | 3,4-Ethylenedioxyphenyl | 1 |
| 79 | OH | p-Methylphenyl | p-Methylphenyl | Methyl | 5-Methoxy-3,4-methylenedioxyphenyl | 1 |
| 80 | OH | p-Methylphenyl | p-Methylphenyl | Methyl | 3,5-Diethylphenyl | 1 |
| 81 | OH | p-Methylphenyl | p-Methylphenyl | Methyl | 3,4-Dimethoxyphenyl | 1 |
| 82 | OH | p-Methylphenyl | p-Methylphenyl | Methyl | 3-Methyl-4-benzyloxyphenyl | 1 |
| 83 | OH | p-Methylphenyl | p-Methylphenyl | Methyl | 3-Benzyloxy-5-methoxyphenyl | 1 |
| 84 | OH | p-Methylphenyl | p-Methylphenyl | Methyl | 3-Benzyloxy-4-methoxyphenyl | 1 |
| 85 | OH | p-Methylphenyl | p-Methylphenyl | Methyl | 3-Hydroxy-4-methoxyphenyl | 1 |
| 86 | OH | p-Methylphenyl | p-Methylphenyl | Methyl | 4-Hydroxy-3-methoxyphenyl | 1 |
| 87 | OH | p-Methylphenyl | p-Methylphenyl | Methyl | 3,5-Bis-(trifluoromethyl)-phenyl | 1 |
| 88 | OH | p-Methylphenyl | p-Methylphenyl | Methyl | 3-Methylphenyl | 1 |
| 89 | OH | p-Methylphenyl | p-Methylphenyl | Methyl | 3-Methoxyphenyl | 1 |
| 90 | OH | p-Methylphenyl | p-Methylphenyl | Methyl | 4-Benzyloxyphenyl | 1 |
| 91 | OH | p-Methylphenyl | p-Methylphenyl | Methyl | 4-Phenoxyphenyl | 1 |
| 92 | OH | p-Methylphenyl | p-Methylphenyl | Methyl | 6-Methylpyridin-2-yl | 1 |
| 93 | OH | p-Methylphenyl | p-Methylphenyl | Methyl | 6-Ethylpyridin-2-yl | 1 |
| 94 | OH | p-Methylphenyl | p-Methylphenyl | Methyl | 6-Methoxypyridin-2-yl | 1 |
| 95 | OH | p-Methylphenyl | p-Methylphenyl | Methyl | 4,6-Dimethylpyridin-2-yl | 1 |
| 96 | OH | p-Methylphenyl | p-Methylphenyl | Methyl | 4,6-Diethylpyridin-2-yl | 1 |
| 97 | OH | p-Methylphenyl | p-Methylphenyl | Methyl | 4-Methyl-6-methoxypyridin-2-yl | 1 |
| 98 | OH | p-Methylphenyl | p-Methylphenyl | Methyl | 6,7-Dihydro-5H-cyclopenta[b]pyridin-2-yl | 1 |
| 99 | OH | p-Methylphenyl | p-Methylphenyl | Methyl | 4,6-Dimethylpyrimidin-2-yl | 1 |
| 100 | OH | p-Methylphenyl | p-Methylphenyl | Methyl | 4-Methoxy-6-methylpyrimidin-2-yl | 1 |
| 101 | OH | p-Methylphenyl | p-Methylphenyl | Methyl | 4,6-Dimethoxypyrimidin-2-yl | 1 |
| 102 | OH | p-Methylphenyl | p-Methylphenyl | Methyl | 4,6-Diethylpyrimidin-2-yl | 1 |
| 103 | OH | p-Methylphenyl | p-Methylphenyl | Methyl | 6,7-Dihydro-5H-cyclopentapyrimidin-2-yl | 1 |
| 104 | OH | p-Methylphenyl | p-Methylphenyl | Methyl | Naphth-2-yl | 1 |
| 105 | OH | p-Methylphenyl | p-Methylphenyl | Methyl | 6,7-Dihydro-5H-cyclopenta[c]pyridin-2-yl | 1 |
| 106 | OH | 4-Methoxy-3-methylphenyl | 4-Methoxy-3-methylphenyl | Methyl | Phenyl | 1 |
| 107 | OH | 4-Methoxy-3-methylphenyl | 4-Methoxy-3-methylphenyl | Methyl | 3,5-Dimethylphenyl | 1 |
| 108 | OH | 4-Methoxy-3-methylphenyl | 4-Methoxy-3-methylphenyl | Methyl | 3,5-Dimethoxyphenyl | 1 |
| 109 | OH | 4-Methoxy-3-methylphenyl | 4-Methoxy-3-methylphenyl | Methyl | 3,4-Methylenedioxyphenyl | 1 |
| 110 | OH | 4-Methoxy-3-methylphenyl | 4-Methoxy-3-methylphenyl | Methyl | 2,3-Dihydro-benzofuran-5-yl | 1 |
| 111 | OH | 4-Methoxy-3-methylphenyl | 4-Methoxy-3-methylphenyl | Methyl | 2,3-Dihydro-1H-inden-5-yl | 1 |
| 112 | OH | 4-Methoxy-3-methylphenyl | 4-Methoxy-3-methylphenyl | Methyl | 3-Methoxy-5-methylphenyl | 1 |
| 113 | OH | 4-Methoxy-3-methylphenyl | 4-Methoxy-3-methylphenyl | Methyl | 3,4-Ethylenedioxyphenyl | 1 |
| 114 | OH | 4-Methoxy-3-methylphenyl | 4-Methoxy-3-methylphenyl | Methyl | 5-Methoxy-3,4-methylenedioxyphenyl | 1 |
| 115 | OH | 4-Methoxy-3-methylphenyl | 4-Methoxy-3-methylphenyl | Methyl | 3,5-Diethylphenyl | 1 |
| 116 | OH | 4-Methoxy-3-methylphenyl | 4-Methoxy-3-methylphenyl | Methyl | 3,4-Dimethoxyphenyl | 1 |
| 117 | OH | 4-Methoxy-3-methylphenyl | 4-Methoxy-3-methylphenyl | Methyl | 3-Methyl-4-benzyloxyphenyl | 1 |
| 118 | OH | 4-Methoxy-3-methylphenyl | 4-Methoxy-3-methylphenyl | Methyl | 3-Benzyloxy-5-methoxyphenyl | 1 |
| 119 | OH | 4-Methoxy-3-methylphenyl | 4-Methoxy-3-methylphenyl | Methyl | 3-Benzyloxy-4-methoxyphenyl | 1 |
| 120 | OH | 4-Methoxy-3-methylphenyl | 4-Methoxy-3-methylphenyl | Methyl | 3-Hydroxy-4-methoxyphenyl | 1 |
| 121 | OH | 4-Methoxy-3-methylphenyl | 4-Methoxy-3-methylphenyl | Methyl | 4-Hydroxy-3-methoxyphenyl | 1 |
| 122 | OH | 4-Methoxy-3-methylphenyl | 4-Methoxy-3-methylphenyl | Methyl | 3,5-Bis-(trifluoromethyl)-phenyl | 1 |
| 123 | OH | 4-Methoxy-3-methylphenyl | 4-Methoxy-3-methylphenyl | Methyl | 3-Methylphenyl | 1 |
| 124 | OH | 4-Methoxy-3-methylphenyl | 4-Methoxy-3-methylphenyl | Methyl | 3-Methoxyphenyl | 1 |
| 125 | OH | 4-Methoxy-3-methylphenyl | 4-Methoxy-3-methylphenyl | Methyl | 4-Benzyloxyphenyl | 1 |
| 126 | OH | 4-Methoxy-3-methylphenyl | 4-Methoxy-3-methylphenyl | Methyl | 4-Phenoxyphenyl | 1 |
| 127 | OH | 4-Methoxy-3-methylphenyl | 4-Methoxy-3-methylphenyl | Methyl | 6-Methylpyridin-2-yl | 1 |
| 128 | OH | 4-Methoxy-3-methylphenyl | 4-Methoxy-3-methylphenyl | Methyl | 6-Ethylpyridin-2-yl | 1 |
| 129 | OH | 4-Methoxy-3-methylphenyl | 4-Methoxy-3-methylphenyl | Methyl | 6-Methoxypyridin-2-yl | 1 |
| 130 | OH | 4-Methoxy-3-methylphenyl | 4-Methoxy-3-methylphenyl | Methyl | 4,6-Dimethylpyridin-2-yl | 1 |
| 131 | OH | 4-Methoxy-3-methylphenyl | 4-Methoxy-3-methylphenyl | Methyl | 4,6-Diethylpyridin-2-yl | 1 |
| 132 | OH | 4-Methoxy-3-methylphenyl | 4-Methoxy-3-methylphenyl | Methyl | 4-Methyl-6-methoxypyridin-2-yl | 1 |
| 133 | OH | 4-Methoxy-3-methylphenyl | 4-Methoxy-3-methylphenyl | Methyl | 6,7-Dihydro-5H-cyclopenta[b]pyridin-2-yl | 1 |
| 134 | OH | 4-Methoxy-3-methylphenyl | 4-Methoxy-3-methylphenyl | Methyl | 4,6-Dimethylpyrimidin-2-yl | 1 |
| 135 | OH | 4-Methoxy-3-methylphenyl | 4-Methoxy-3-methylphenyl | Methyl | 4-Methoxy-6-methylpyrimidin-2-yl | 1 |
| 136 | OH | 4-Methoxy-3-methylphenyl | 4-Methoxy-3-methylphenyl | Methyl | 4,6-Dimethoxypyrimidin-2-yl | 1 |
| 137 | OH | 4-Methoxy-3-methylphenyl | 4-Methoxy-3-methylphenyl | Methyl | 4,6-Diethylpyrimidin-2-yl | 1 |
| 138 | OH | 4-Methoxy-3-methylphenyl | 4-Methoxy-3-methylphenyl | Methyl | 6,7-Dihydro-5H-cyclopentapyrimidin-2-yl | 1 |
| 139 | OH | 4-Methoxy-3-methylphenyl | 4-Methoxy-3-methylphenyl | Methyl | Naphth-2-yl | 1 |
| 140 | OH | 4-Methoxy-3-methylphenyl | 4-Methoxy-3-methylphenyl | Methyl | 6,7-Dihydro-5H-cyclopenta[c]pyridin-2-yl | 1 |
| 141 | OH | Phenyl | Phenyl | Ethyl | Phenyl | 1 |
| 142 | OH | Phenyl | Phenyl | Ethyl | 3,5-Dimethylphenyl | 1 |

-continued

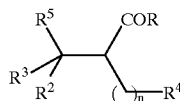

| No. | R | R² | R³ | R⁵ | R⁴ | n |
|---|---|---|---|---|---|---|
| 143 | OH | Phenyl | Phenyl | Ethyl | 3,5-Dimethoxyphenyl | 1 |
| 144 | OH | Phenyl | Phenyl | Ethyl | 3,4-Methylenedioxyphenyl | 1 |
| 145 | OH | Phenyl | Phenyl | Ethyl | 2,3-Dihydro-benzofuran-5-yl | 1 |
| 146 | OH | Phenyl | Phenyl | Ethyl | 2,3-Dihydro-1H-inden-5-yl | 1 |
| 147 | OH | Phenyl | Phenyl | Ethyl | 3-Methoxy-5-methylphenyl | 1 |
| 148 | OH | Phenyl | Phenyl | Ethyl | 3,4-Ethylenedioxyphenyl | 1 |
| 149 | OH | Phenyl | Phenyl | Ethyl | 5-Methoxy-3,4-methylenedioxyphenyl | 1 |
| 150 | OH | Phenyl | Phenyl | Ethyl | 3,5-Diethylphenyl | 1 |
| 151 | OH | Phenyl | Phenyl | Ethyl | 3,4-Dimethoxyphenyl | 1 |
| 152 | OH | Phenyl | Phenyl | Ethyl | 3-Methyl-4-benzyloxyphenyl | 1 |
| 153 | OH | Phenyl | Phenyl | Ethyl | 3-Benzyloxy-5-methoxyphenyl | 1 |
| 154 | OH | Phenyl | Phenyl | Ethyl | 3-Benzyloxy-4-methoxyphenyl | 1 |
| 155 | OH | Phenyl | Phenyl | Ethyl | 3-Hydroxy-4-methoxyphenyl | 1 |
| 156 | OH | Phenyl | Phenyl | Ethyl | 4-Hydroxy-3-methoxyphenyl | 1 |
| 157 | OH | Phenyl | Phenyl | Ethyl | 3,5-Bis-(trifluoromethyl)-phenyl | 1 |
| 158 | OH | Phenyl | Phenyl | Ethyl | 3-Methylphenyl | 1 |
| 159 | OH | Phenyl | Phenyl | Ethyl | 3-Methoxyphenyl | 1 |
| 160 | OH | Phenyl | Phenyl | Ethyl | 4-Benzyloxyphenyl | 1 |
| 161 | OH | Phenyl | Phenyl | Ethyl | 4-Phenoxyphenyl | 1 |
| 162 | OH | Phenyl | Phenyl | Ethyl | 6-Methylpyridin-2-yl | 1 |
| 163 | OH | Phenyl | Phenyl | Ethyl | 6-Ethylpyridin-2-yl | 1 |
| 164 | OH | Phenyl | Phenyl | Ethyl | 6-Methoxypyridin-2-yl | 1 |
| 165 | OH | Phenyl | Phenyl | Ethyl | 4,6-Dimethylpyridin-2-yl | 1 |
| 166 | OH | Phenyl | Phenyl | Ethyl | 4,6-Diethylpyridin-2-yl | 1 |
| 167 | OH | Phenyl | Phenyl | Ethyl | 4-Methyl-6-methoxypyridin-2-yl | 1 |
| 168 | OH | Phenyl | Phenyl | Ethyl | 6,7-Dihydro-5H-cyclopenta[b]pyridin-2-yl | 1 |
| 169 | OH | Phenyl | Phenyl | Ethyl | 4,6-Dimethylpyrimidin-2-yl | 1 |
| 170 | OH | Phenyl | Phenyl | Ethyl | 4-Methoxy-6-methylpyrimidin-2-yl | 1 |
| 171 | OH | Phenyl | Phenyl | Ethyl | 4,6-Dimethoxypyrimidin-2-yl | 1 |
| 172 | OH | Phenyl | Phenyl | Ethyl | 4,6-Diethylpyrimidin-2-yl | 1 |
| 173 | OH | Phenyl | Phenyl | Ethyl | 6,7-Dihydro-5H-cyclopentapyrimidin-2-yl | 1 |
| 174 | OH | Phenyl | Phenyl | Ethyl | Naphth-2-yl | 1 |
| 175 | OH | Phenyl | Phenyl | Ethyl | 6,7-Dihydro-5H-cyclopenta[c]pyridin-2-yl | 1 |
| 176 | OH | p-Methoxyphenyl | p-Methoxyphenyl | Ethyl | Phenyl | 1 |
| 177 | OH | p-Methoxyphenyl | p-Methoxyphenyl | Ethyl | 3,5-Dimethylphenyl | 1 |
| 178 | OH | p-Methoxyphenyl | p-Methoxyphenyl | Ethyl | 3,5-Dimethoxyphenyl | 1 |
| 179 | OH | p-Methoxyphenyl | p-Methoxyphenyl | Ethyl | 3,4-Methylenedioxyphenyl | 1 |
| 180 | OH | p-Methoxyphenyl | p-Methoxyphenyl | Ethyl | 2,3-Dihydro-benzofuran-5-yl | 1 |
| 181 | OH | p-Methoxyphenyl | p-Methoxyphenyl | Ethyl | 2,3-Dihydro-1H-inden-5-yl | 1 |
| 182 | OH | p-Methoxyphenyl | p-Methoxyphenyl | Ethyl | 3-Methoxy-5-methylphenyl | 1 |
| 183 | OH | p-Methoxyphenyl | p-Methoxyphenyl | Ethyl | 3,4-Ethylenedioxyphenyl | 1 |
| 184 | OH | p-Methoxyphenyl | p-Methoxyphenyl | Ethyl | 5-Methoxy-3,4-methylenedioxyphenyl | 1 |
| 185 | OH | p-Methoxyphenyl | p-Methoxyphenyl | Ethyl | 3,5-Diethylphenyl | 1 |
| 186 | OH | p-Methoxyphenyl | p-Methoxyphenyl | Ethyl | 3,4-Dimethoxyphenyl | 1 |
| 187 | OH | p-Methoxyphenyl | p-Methoxyphenyl | Ethyl | 3-Methyl-4-benzyloxyphenyl | 1 |
| 188 | OH | p-Methoxyphenyl | p-Methoxyphenyl | Ethyl | 3-Benzyloxy-5-methoxyphenyl | 1 |
| 189 | OH | p-Methoxyphenyl | p-Methoxyphenyl | Ethyl | 3-Benzyloxy-4-methoxyphenyl | 1 |
| 190 | OH | p-Methoxyphenyl | p-Methoxyphenyl | Ethyl | 3-Hydroxy-4-methoxyphenyl | 1 |
| 191 | OH | p-Methoxyphenyl | p-Methoxyphenyl | Ethyl | 4-Hydroxy-3-methoxyphenyl | 1 |
| 192 | OH | p-Methoxyphenyl | p-Methoxyphenyl | Ethyl | 3,5-Bis-(trifluoromethyl)-phenyl | 1 |
| 193 | OH | p-Methoxyphenyl | p-Methoxyphenyl | Ethyl | 3-Methylphenyl | 1 |
| 194 | OH | p-Methoxyphenyl | p-Methoxyphenyl | Ethyl | 3-Methoxyphenyl | 1 |
| 195 | OH | p-Methoxyphenyl | p-Methoxyphenyl | Ethyl | 4-Benzyloxyphenyl | 1 |
| 196 | OH | p-Methoxyphenyl | p-Methoxyphenyl | Ethyl | 4-Phenoxyphenyl | 1 |
| 197 | OH | p-Methoxyphenyl | p-Methoxyphenyl | Ethyl | 6-Methylpyridin-2-yl | 1 |
| 198 | OH | p-Methoxyphenyl | p-Methoxyphenyl | Ethyl | 6-Ethylpyridin-2-yl | 1 |
| 199 | OH | p-Methoxyphenyl | p-Methoxyphenyl | Ethyl | 6-Methoxypyridin-2-yl | 1 |
| 200 | OH | p-Methoxyphenyl | p-Methoxyphenyl | Ethyl | 4,6-Dimethylpyridin-2-yl | 1 |
| 201 | OH | p-Methoxyphenyl | p-Methoxyphenyl | Ethyl | 4,6-Diethylpyridin-2-yl | 1 |
| 202 | OH | p-Methoxyphenyl | p-Methoxyphenyl | Ethyl | 4-Methyl-6-methoxypyridin-2-yl | 1 |
| 203 | OH | p-Methoxyphenyl | p-Methoxyphenyl | Ethyl | 6,7-Dihydro-5H-cyclopenta[b]pyridin-2-yl | 1 |
| 204 | OH | p-Methoxyphenyl | p-Methoxyphenyl | Ethyl | 4,6-Dimethylpyrimidin-2-yl | 1 |
| 205 | OH | p-Methoxyphenyl | p-Methoxyphenyl | Ethyl | 4-Methoxy-6-methylpyrimidin-2-yl | 1 |
| 206 | OH | p-Methoxyphenyl | p-Methoxyphenyl | Ethyl | 4,6-Dimethoxypyrimidin-2-yl | 1 |
| 207 | OH | p-Methoxyphenyl | p-Methoxyphenyl | Ethyl | 4,6-Diethylpyrimidin-2-yl | 1 |
| 208 | OH | p-Methoxyphenyl | p-Methoxyphenyl | Ethyl | 6,7-Dihydro-5H-cyclopentapyrimidin-2-yl | 1 |
| 209 | OH | p-Methoxyphenyl | p-Methoxyphenyl | Ethyl | Naphth-2-yl | 1 |
| 210 | OH | p-Methoxyphenyl | p-Methoxyphenyl | Ethyl | 6,7-Dihydro-5H-cyclopenta[c]pyridin-2-yl | 1 |
| 211 | OH | p-Methylphenyl | p-Methylphenyl | Ethyl | Phenyl | 1 |
| 212 | OH | p-Methylphenyl | p-Methylphenyl | Ethyl | 3,5-Dimethylphenyl | 1 |
| 213 | OH | p-Methylphenyl | p-Methylphenyl | Ethyl | 3,5-Dimethoxyphenyl | 1 |

-continued

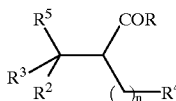

| No. | R | R² | R³ | R⁵ | R⁴ | n |
|---|---|---|---|---|---|---|
| 214 | OH | p-Methylphenyl | p-Methylphenyl | Ethyl | 3,4-Methylenedioxyphenyl | 1 |
| 215 | OH | p-Methylphenyl | p-Methylphenyl | Ethyl | 2,3-Dihydro-benzofuran-5-yl | 1 |
| 216 | OH | p-Methylphenyl | p-Methylphenyl | Ethyl | 2,3-Dihydro-1H-inden-5-yl | 1 |
| 217 | OH | p-Methylphenyl | p-Methylphenyl | Ethyl | 3-Methoxy-5-methylphenyl | 1 |
| 218 | OH | p-Methylphenyl | p-Methylphenyl | Ethyl | 3,4-Ethylenedioxyphenyl | 1 |
| 219 | OH | p-Methylphenyl | p-Methylphenyl | Ethyl | 5-Methoxy-3,4-methylenedioxyphenyl | 1 |
| 220 | OH | p-Methylphenyl | p-Methylphenyl | Ethyl | 3,5-Diethylphenyl | 1 |
| 221 | OH | p-Methylphenyl | p-Methylphenyl | Ethyl | 3,4-Dimethoxyphenyl | 1 |
| 222 | OH | p-Methylphenyl | p-Methylphenyl | Ethyl | 3-Methyl-4-benzyloxyphenyl | 1 |
| 223 | OH | p-Methylphenyl | p-Methylphenyl | Ethyl | 3-Benzyloxy-5-methoxyphenyl | 1 |
| 224 | OH | p-Methylphenyl | p-Methylphenyl | Ethyl | 3-Benzyloxy-4-methoxyphenyl | 1 |
| 225 | OH | p-Methylphenyl | p-Methylphenyl | Ethyl | 3-Hydroxy-4-methoxyphenyl | 1 |
| 226 | OH | p-Methylphenyl | p-Methylphenyl | Ethyl | 4-Hydroxy-3-methoxyphenyl | 1 |
| 227 | OH | p-Methylphenyl | p-Methylphenyl | Ethyl | 3,5-Bis-(trifluoromethyl)-phenyl | 1 |
| 228 | OH | p-Methylphenyl | p-Methylphenyl | Ethyl | 3-Methylphenyl | 1 |
| 229 | OH | p-Methylphenyl | p-Methylphenyl | Ethyl | 3-Methoxyphenyl | 1 |
| 230 | OH | p-Methylphenyl | p-Methylphenyl | Ethyl | 4-Benzyloxyphenyl | 1 |
| 231 | OH | p-Methylphenyl | p-Methylphenyl | Ethyl | 4-Phenoxyphenyl | 1 |
| 232 | OH | p-Methylphenyl | p-Methylphenyl | Ethyl | 6-Methylpyridin-2-yl | 1 |
| 233 | OH | p-Methylphenyl | p-Methylphenyl | Ethyl | 6-Ethylpyridin-2-yl | 1 |
| 234 | OH | p-Methylphenyl | p-Methylphenyl | Ethyl | 6-Methoxypyridin-2-yl | 1 |
| 235 | OH | p-Methylphenyl | p-Methylphenyl | Ethyl | 4,6-Dimethylpyridin-2-yl | 1 |
| 236 | OH | p-Methylphenyl | p-Methylphenyl | Ethyl | 4,6-Diethylpyridin-2-yl | 1 |
| 237 | OH | p-Methylphenyl | p-Methylphenyl | Ethyl | 4-Methyl-6-methoxypyridin-2-yl | 1 |
| 238 | OH | p-Methylphenyl | p-Methylphenyl | Ethyl | 6,7-Dihydro-5H-cyclopenta[b]pyridin-2-yl | 1 |
| 239 | OH | p-Methylphenyl | p-Methylphenyl | Ethyl | 4,6-Dimethylpyrimidin-2-yl | 1 |
| 240 | OH | p-Methylphenyl | p-Methylphenyl | Ethyl | 4-Methoxy-6-methylpyrimidin-2-yl | 1 |
| 241 | OH | p-Methylphenyl | p-Methylphenyl | Ethyl | 4,6-Dimethoxypyrimidin-2-yl | 1 |
| 242 | OH | p-Methylphenyl | p-Methylphenyl | Ethyl | 4,6-Diethylpyrimidin-2-yl | 1 |
| 243 | OH | p-Methylphenyl | p-Methylphenyl | Ethyl | 6,7-Dihydro-5H-cyclopentapyrimidin-2-yl | 1 |
| 244 | OH | p-Methylphenyl | p-Methylphenyl | Ethyl | Naphth-2-yl | 1 |
| 245 | OH | p-Methylphenyl | p-Methylphenyl | Ethyl | 6,7-Dihydro-5H-cyclopenta[c]pyridin-2-yl | 1 |
| 246 | OH | 4-Methoxy-3-methylphenyl | 4-Methoxy-3-methylphenyl | Ethyl | Phenyl | 1 |
| 247 | OH | 4-Methoxy-3-methylphenyl | 4-Methoxy-3-methylphenyl | Ethyl | 3,5-Dimethylphenyl | 1 |
| 248 | OH | 4-Methoxy-3-methylphenyl | 4-Methoxy-3-methylphenyl | Ethyl | 3,5-Dimethoxyphenyl | 1 |
| 249 | OH | 4-Methoxy-3-methylphenyl | 4-Methoxy-3-methylphenyl | Ethyl | 3,4-Methylenedioxyphenyl | 1 |
| 250 | OH | 4-Methoxy-3-methylphenyl | 4-Methoxy-3-methylphenyl | Ethyl | 2,3-Dihydro-benzofuran-5-yl | 1 |
| 251 | OH | 4-Methoxy-3-methylphenyl | 4-Methoxy-3-methylphenyl | Ethyl | 2,3-Dihydro-1H-inden-5-yl | 1 |
| 252 | OH | 4-Methoxy-3-methylphenyl | 4-Methoxy-3-methylphenyl | Ethyl | 3-Methoxy-5-methylphenyl | 1 |
| 253 | OH | 4-Methoxy-3-methylphenyl | 4-Methoxy-3-methylphenyl | Ethyl | 3,4-Ethylenedioxyphenyl | 1 |
| 254 | OH | 4-Methoxy-3-methylphenyl | 4-Methoxy-3-methylphenyl | Ethyl | 5-Methoxy-3,4-methylenedioxyphenyl | 1 |
| 255 | OH | 4-Methoxy-3-methylphenyl | 4-Methoxy-3-methylphenyl | Ethyl | 3,5-Diethylphenyl | 1 |
| 256 | OH | 4-Methoxy-3-methylphenyl | 4-Methoxy-3-methylphenyl | Ethyl | 3,4-Dimethoxyphenyl | 1 |
| 257 | OH | 4-Methoxy-3-methylphenyl | 4-Methoxy-3-methylphenyl | Ethyl | 3-Methyl-4-benzyloxyphenyl | 1 |
| 258 | OH | 4-Methoxy-3-methylphenyl | 4-Methoxy-3-methylphenyl | Ethyl | 3-Benzyloxy-5-methoxyphenyl | 1 |
| 259 | OH | 4-Methoxy-3-methylphenyl | 4-Methoxy-3-methylphenyl | Ethyl | 3-Benzyloxy-4-methoxyphenyl | 1 |
| 260 | OH | 4-Methoxy-3-methylphenyl | 4-Methoxy-3-methylphenyl | Ethyl | 3-Hydroxy-4-methoxyphenyl | 1 |
| 261 | OH | 4-Methoxy-3-methylphenyl | 4-Methoxy-3-methylphenyl | Ethyl | 4-Hydroxy-3-methoxyphenyl | 1 |
| 262 | OH | 4-Methoxy-3-methylphenyl | 4-Methoxy-3-methylphenyl | Ethyl | 3,5-Bis-(trifluoromethyl)-phenyl | 1 |
| 263 | OH | 4-Methoxy-3-methylphenyl | 4-Methoxy-3-methylphenyl | Ethyl | 3-Methylphenyl | 1 |
| 264 | OH | 4-Methoxy-3-methylphenyl | 4-Methoxy-3-methylphenyl | Ethyl | 3-Methoxyphenyl | 1 |
| 265 | OH | 4-Methoxy-3-methylphenyl | 4-Methoxy-3-methylphenyl | Ethyl | 4-Benzyloxyphenyl | 1 |
| 266 | OH | 4-Methoxy-3-methylphenyl | 4-Methoxy-3-methylphenyl | Ethyl | 4-Phenoxyphenyl | 1 |
| 267 | OH | 4-Methoxy-3-methylphenyl | 4-Methoxy-3-methylphenyl | Ethyl | 6-Methylpyridin-2-yl | 1 |
| 268 | OH | 4-Methoxy-3-methylphenyl | 4-Methoxy-3-methylphenyl | Ethyl | 6-Ethylpyridin-2-yl | 1 |
| 269 | OH | 4-Methoxy-3-methylphenyl | 4-Methoxy-3-methylphenyl | Ethyl | 6-Methoxypyridin-2-yl | 1 |
| 270 | OH | 4-Methoxy-3-methylphenyl | 4-Methoxy-3-methylphenyl | Ethyl | 4,6-Dimethylpyridin-2-yl | 1 |
| 271 | OH | 4-Methoxy-3-methylphenyl | 4-Methoxy-3-methylphenyl | Ethyl | 4,6-Diethylpyridin-2-yl | 1 |
| 272 | OH | 4-Methoxy-3-methylphenyl | 4-Methoxy-3-methylphenyl | Ethyl | 4-Methyl-6-methoxypyridin-2-yl | 1 |
| 273 | OH | 4-Methoxy-3-methylphenyl | 4-Methoxy-3-methylphenyl | Ethyl | 6,7-Dihydro-5H-cyclopenta[b]pyridin-2-yl | 1 |
| 274 | OH | 4-Methoxy-3-methylphenyl | 4-Methoxy-3-methylphenyl | Ethyl | 4,6-Dimethylpyrimidin-2-yl | 1 |
| 275 | OH | 4-Methoxy-3-methylphenyl | 4-Methoxy-3-methylphenyl | Ethyl | 4-Methoxy-6-methylpyrimidin-2-yl | 1 |
| 276 | OH | 4-Methoxy-3-methylphenyl | 4-Methoxy-3-methylphenyl | Ethyl | 4,6-Dimethoxypyrimidin-2-yl | 1 |
| 277 | OH | 4-Methoxy-3-methylphenyl | 4-Methoxy-3-methylphenyl | Ethyl | 4,6-Diethylpyrimidin-2-yl | 1 |
| 278 | OH | 4-Methoxy-3-methylphenyl | 4-Methoxy-3-methylphenyl | Ethyl | 6,7-Dihydro-5H-cyclopentapyrimidin-2-yl | 1 |
| 279 | OH | 4-Methoxy-3-methylphenyl | 4-Methoxy-3-methylphenyl | Ethyl | Naphth-2-yl | 1 |
| 280 | OH | 4-Methoxy-3-methylphenyl | 4-Methoxy-3-methylphenyl | Ethyl | 6,7-Dihydro-5H-cyclopenta[c]pyridin-2-yl | 1 |
| 281 | OH | Phenyl | Phenyl | Propyl | Phenyl | 1 |
| 282 | OH | Phenyl | Phenyl | Propyl | 3,5-Dimethylphenyl | 1 |
| 283 | OH | Phenyl | Phenyl | Propyl | 3,5-Dimethoxyphenyl | 1 |
| 284 | OH | Phenyl | Phenyl | Propyl | 3,4-Methylenedioxyphenyl | 1 |

-continued

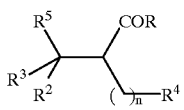

| No. | R | R² | R³ | R⁵ | R⁴ | n |
|---|---|---|---|---|---|---|
| 285 | OH | Phenyl | Phenyl | Propyl | 2,3-Dihydro-benzofuran-5-yl | 1 |
| 286 | OH | Phenyl | Phenyl | Propyl | 2,3-Dihydro-1H-inden-5-yl | 1 |
| 287 | OH | Phenyl | Phenyl | Propyl | 3-Methoxy-5-methylphenyl | 1 |
| 288 | OH | Phenyl | Phenyl | Propyl | 3,4-Ethylenedioxyphenyl | 1 |
| 289 | OH | Phenyl | Phenyl | Propyl | 5-Methoxy-3,4-methylenedioxyphenyl | 1 |
| 290 | OH | Phenyl | Phenyl | Propyl | 3,5-Diethylphenyl | 1 |
| 291 | OH | Phenyl | Phenyl | Propyl | 3,4-Dimethoxyphenyl | 1 |
| 292 | OH | Phenyl | Phenyl | Propyl | 3-Methyl-4-benzyloxyphenyl | 1 |
| 293 | OH | Phenyl | Phenyl | Propyl | 3-Benzyloxy-5-methoxyphenyl | 1 |
| 294 | OH | Phenyl | Phenyl | Propyl | 3-Benzyloxy-4-methoxyphenyl | 1 |
| 295 | OH | Phenyl | Phenyl | Propyl | 3-Hydroxy-4-methoxyphenyl | 1 |
| 296 | OH | Phenyl | Phenyl | Propyl | 4-Hydroxy-3-methoxyphenyl | 1 |
| 297 | OH | Phenyl | Phenyl | Propyl | 3,5-Bis-(trifluoromethyl)-phenyl | 1 |
| 298 | OH | Phenyl | Phenyl | Propyl | 3-Methylphenyl | 1 |
| 299 | OH | Phenyl | Phenyl | Propyl | 3-Methoxyphenyl | 1 |
| 300 | OH | Phenyl | Phenyl | Propyl | 4-Benzyloxyphenyl | 1 |
| 301 | OH | Phenyl | Phenyl | Propyl | 4-Phenoxyphenyl | 1 |
| 302 | OH | Phenyl | Phenyl | Propyl | 6-Methylpyridin-2-yl | 1 |
| 303 | OH | Phenyl | Phenyl | Propyl | 6-Ethylpyridin-2-yl | 1 |
| 304 | OH | Phenyl | Phenyl | Propyl | 6-Methoxypyridin-2-yl | 1 |
| 305 | OH | Phenyl | Phenyl | Propyl | 4,6-Dimethylpyridin-2-yl | 1 |
| 306 | OH | Phenyl | Phenyl | Propyl | 4,6-Diethylpyridin-2-yl | 1 |
| 307 | OH | Phenyl | Phenyl | Propyl | 4-Methyl-6-methoxypyridin-2-yl | 1 |
| 308 | OH | Phenyl | Phenyl | Propyl | 6,7-Dihydro-5H-cyclopenta[b]pyridin-2-yl | 1 |
| 309 | OH | Phenyl | Phenyl | Propyl | 4,6-Dimethylpyrimidin-2-yl | 1 |
| 310 | OH | Phenyl | Phenyl | Propyl | 4-Methoxy-6-methylpyrimidin-2-yl | 1 |
| 311 | OH | Phenyl | Phenyl | Propyl | 4,6-Dimethoxypyrimidin-2-yl | 1 |
| 312 | OH | Phenyl | Phenyl | Propyl | 4,6-Diethylpyrimidin-2-yl | 1 |
| 313 | OH | Phenyl | Phenyl | Propyl | 6,7-Dihydro-5H-cyclopentapyrimidin-2-yl | 1 |
| 314 | OH | Phenyl | Phenyl | Propyl | Naphth-2-yl | 1 |
| 315 | OH | Phenyl | Phenyl | Propyl | 6,7-Dihydro-5H-cyclopenta[c]pyridin-2-yl | 1 |
| 316 | OH | p-Methoxyphenyl | p-Methoxyphenyl | Propyl | Phenyl | 1 |
| 317 | OH | p-Methoxyphenyl | p-Methoxyphenyl | Propyl | 3,5-Dimethylphenyl | 1 |
| 318 | OH | p-Methoxyphenyl | p-Methoxyphenyl | Propyl | 3,5-Dimethoxyphenyl | 1 |
| 319 | OH | p-Methoxyphenyl | p-Methoxyphenyl | Propyl | 3,4-Methylenedioxyphenyl | 1 |
| 320 | OH | p-Methoxyphenyl | p-Methoxyphenyl | Propyl | 2,3-Dihydro-benzofuran-5-yl | 1 |
| 321 | OH | p-Methoxyphenyl | p-Methoxyphenyl | Propyl | 2,3-Dihydro-1H-inden-5-yl | 1 |
| 322 | OH | p-Methoxyphenyl | p-Methoxyphenyl | Propyl | 3-Methoxy-5-methylphenyl | 1 |
| 323 | OH | p-Methoxyphenyl | p-Methoxyphenyl | Propyl | 3,4-Ethylenedioxyphenyl | 1 |
| 324 | OH | p-Methoxyphenyl | p-Methoxyphenyl | Propyl | 5-Methoxy-3,4-methylenedioxyphenyl | 1 |
| 325 | OH | p-Methoxyphenyl | p-Methoxyphenyl | Propyl | 3,5-Diethylphenyl | 1 |
| 326 | OH | p-Methoxyphenyl | p-Methoxyphenyl | Propyl | 3,4-Dimethoxyphenyl | 1 |
| 327 | OH | p-Methoxyphenyl | p-Methoxyphenyl | Propyl | 3-Methyl-4-benzyloxyphenyl | 1 |
| 328 | OH | p-Methoxyphenyl | p-Methoxyphenyl | Propyl | 3-Benzyloxy-5-methoxyphenyl | 1 |
| 329 | OH | p-Methoxyphenyl | p-Methoxyphenyl | Propyl | 3-Benzyloxy-4-methoxyphenyl | 1 |
| 330 | OH | p-Methoxyphenyl | p-Methoxyphenyl | Propyl | 3-Hydroxy-4-methoxyphenyl | 1 |
| 331 | OH | p-Methoxyphenyl | p-Methoxyphenyl | Propyl | 4-Hydroxy-3-methoxyphenyl | 1 |
| 332 | OH | p-Methoxyphenyl | p-Methoxyphenyl | Propyl | 3,5-Bis-(trifluoromethyl)-phenyl | 1 |
| 333 | OH | p-Methoxyphenyl | p-Methoxyphenyl | Propyl | 3-Methylphenyl | 1 |
| 334 | OH | p-Methoxyphenyl | p-Methoxyphenyl | Propyl | 3-Methoxyphenyl | 1 |
| 335 | OH | p-Methoxyphenyl | p-Methoxyphenyl | Propyl | 4-Benzyloxyphenyl | 1 |
| 336 | OH | p-Methoxyphenyl | p-Methoxyphenyl | Propyl | 4-Phenoxyphenyl | 1 |
| 337 | OH | p-Methoxyphenyl | p-Methoxyphenyl | Propyl | 6-Methylpyridin-2-yl | 1 |
| 338 | OH | p-Methoxyphenyl | p-Methoxyphenyl | Propyl | 6-Ethylpyridin-2-yl | 1 |
| 339 | OH | p-Methoxyphenyl | p-Methoxyphenyl | Propyl | 6-Methoxypyridin-2-yl | 1 |
| 340 | OH | p-Methoxyphenyl | p-Methoxyphenyl | Propyl | 4,6-Dimethylpyridin-2-yl | 1 |
| 341 | OH | p-Methoxyphenyl | p-Methoxyphenyl | Propyl | 4,6-Diethylpyridin-2-yl | 1 |
| 342 | OH | p-Methoxyphenyl | p-Methoxyphenyl | Propyl | 4-Methyl-6-methoxypyridin-2-yl | 1 |
| 343 | OH | p-Methoxyphenyl | p-Methoxyphenyl | Propyl | 6,7-Dihydro-5H-cyclopenta-[b]pyridin-2-yl | 1 |
| 344 | OH | p-Methoxyphenyl | p-Methoxyphenyl | Propyl | 4,6-Dimethylpyrimidin-2-yl | 1 |
| 345 | OH | p-Methoxyphenyl | p-Methoxyphenyl | Propyl | 4-Methoxy-6-methylpyrimidin-2-yl | 1 |
| 346 | OH | p-Methoxyphenyl | p-Methoxyphenyl | Propyl | 4,6-Dimethoxypyrimidin-2-yl | 1 |
| 347 | OH | p-Methoxyphenyl | p-Methoxyphenyl | Propyl | 4,6-Diethylpyrimidin-2-yl | 1 |
| 348 | OH | p-Methoxyphenyl | p-Methoxyphenyl | Propyl | 6,7-Dihydro-5H-cyclopentapyrimidin-2-yl | 1 |
| 349 | OH | p-Methoxyphenyl | p-Methoxyphenyl | Propyl | Naphth-2-yl | 1 |
| 350 | OH | p-Methoxyphenyl | p-Methoxyphenyl | Propyl | 6,7-Dihydro-5H-cyclopenta[c]pyridin-2-yl | 1 |
| 351 | OH | p-Methylphenyl | p-Methylphenyl | Propyl | Phenyl | 1 |
| 352 | OH | p-Methylphenyl | p-Methylphenyl | Propyl | 3,5-Dimethylphenyl | 1 |
| 353 | OH | p-Methylphenyl | p-Methylphenyl | Propyl | 3,5-Dimethoxyphenyl | 1 |
| 354 | OH | p-Methylphenyl | p-Methylphenyl | Propyl | 3,4-Methylenedioxyphenyl | 1 |
| 355 | OH | p-Methylphenyl | p-Methylphenyl | Propyl | 2,3-Dihydro-benzofuran-5-yl | 1 |

-continued

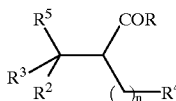

| No. | R | R² | R³ | R⁵ | R⁴ | n |
|---|---|---|---|---|---|---|
| 356 | OH | p-Methylphenyl | p-Methylphenyl | Propyl | 2,3-Dihydro-1H-inden-5-yl | 1 |
| 357 | OH | p-Methylphenyl | p-Methylphenyl | Propyl | 3-Methoxy-5-methylphenyl | 1 |
| 358 | OH | p-Methylphenyl | p-Methylphenyl | Propyl | 3,4-Ethylenedioxyphenyl | 1 |
| 359 | OH | p-Methylphenyl | p-Methylphenyl | Propyl | 5-Methoxy-3,4-methylenedioxyphenyl | 1 |
| 360 | OH | p-Methylphenyl | p-Methylphenyl | Propyl | 3,5-Diethylphenyl | 1 |
| 361 | OH | p-Methylphenyl | p-Methylphenyl | Propyl | 3,4-Dimethoxyphenyl | 1 |
| 362 | OH | p-Methylphenyl | p-Methylphenyl | Propyl | 3-Methyl-4-benzyloxyphenyl | 1 |
| 363 | OH | p-Methylphenyl | p-Methylphenyl | Propyl | 3-Benzyloxy-5-methoxyphenyl | 1 |
| 364 | OH | p-Methylphenyl | p-Methylphenyl | Propyl | 3-Benzyloxy-4-methoxyphenyl | 1 |
| 365 | OH | p-Methylphenyl | p-Methylphenyl | Propyl | 3-Hydroxy-4-methoxyphenyl | 1 |
| 366 | OH | p-Methylphenyl | p-Methylphenyl | Propyl | 4-Hydroxy-3-methoxyphenyl | 1 |
| 367 | OH | p-Methylphenyl | p-Methylphenyl | Propyl | 3,5-Bis-(trifluoromethyl)-phenyl | 1 |
| 368 | OH | p-Methylphenyl | p-Methylphenyl | Propyl | 3-Methylphenyl | 1 |
| 369 | OH | p-Methylphenyl | p-Methylphenyl | Propyl | 3-Methoxyphenyl | 1 |
| 370 | OH | p-Methylphenyl | p-Methylphenyl | Propyl | 4-Benzyloxyphenyl | 1 |
| 371 | OH | p-Methylphenyl | p-Methylphenyl | Propyl | 4-Phenoxyphenyl | 1 |
| 372 | OH | p-Methylphenyl | p-Methylphenyl | Propyl | 6-Methylpyridin-2-yl | 1 |
| 373 | OH | p-Methylphenyl | p-Methylphenyl | Propyl | 6-Ethylpyridin-2-yl | 1 |
| 374 | OH | p-Methylphenyl | p-Methylphenyl | Propyl | 6-Methoxypyridin-2-yl | 1 |
| 375 | OH | p-Methylphenyl | p-Methylphenyl | Propyl | 4,6-Dimethylpyridin-2-yl | 1 |
| 376 | OH | p-Methylphenyl | p-Methylphenyl | Propyl | 4,6-Diethylpyridin-2-yl | 1 |
| 377 | OH | p-Methylphenyl | p-Methylphenyl | Propyl | 4-Methyl-6-methoxypyridin-2-yl | 1 |
| 378 | OH | p-Methylphenyl | p-Methylphenyl | Propyl | 6,7-Dihydro-5H-cyclopenta[b]pyridin-2-yl | 1 |
| 379 | OH | p-Methylphenyl | p-Methylphenyl | Propyl | 4,6-Dimethylpyrimidin-2-yl | 1 |
| 380 | OH | p-Methylphenyl | p-Methylphenyl | Propyl | 4-Methoxy-6-methylpyrimidin-2-yl | 1 |
| 381 | OH | p-Methylphenyl | p-Methylphenyl | Propyl | 4,6-Dimethoxypyrimidin-2-yl | 1 |
| 382 | OH | p-Methylphenyl | p-Methylphenyl | Propyl | 4,6-Diethylpyrimidin-2-yl | 1 |
| 383 | OH | p-Methylphenyl | p-Methylphenyl | Propyl | 6,7-Dihydro-5H-cyclopentapyrimidin-2-yl | 1 |
| 384 | OH | p-Methylphenyl | p-Methylphenyl | Propyl | Naphth-2-yl | 1 |
| 385 | OH | p-Methylphenyl | p-Methylphenyl | Propyl | 6,7-Dihydro-5H-cyclopenta[c]pyridin-2-yl | 1 |
| 386 | OH | 4-Methoxy-3-methylphenyl | 4-Methoxy-3-methylphenyl | Propyl | Phenyl | 1 |
| 387 | OH | 4-Methoxy-3-methylphenyl | 4-Methoxy-3-methylphenyl | Propyl | 3,5-Dimethylphenyl | 1 |
| 388 | OH | 4-Methoxy-3-methylphenyl | 4-Methoxy-3-methylphenyl | Propyl | 3,5-Dimethoxyphenyl | 1 |
| 389 | OH | 4-Methoxy-3-methylphenyl | 4-Methoxy-3-methylphenyl | Propyl | 3,4-Methylenedioxyphenyl | 1 |
| 390 | OH | 4-Methoxy-3-methylphenyl | 4-Methoxy-3-methylphenyl | Propyl | 2,3-Dihydro-benzofuran-5-yl | 1 |
| 391 | OH | 4-Methoxy-3-methylphenyl | 4-Methoxy-3-methylphenyl | Propyl | 2,3-Dihydro-1H-inden-5-yl | 1 |
| 392 | OH | 4-Methoxy-3-methylphenyl | 4-Methoxy-3-methylphenyl | Propyl | 3-Methoxy-5-methylphenyl | 1 |
| 393 | OH | 4-Methoxy-3-methylphenyl | 4-Methoxy-3-methylphenyl | Propyl | 3,4-Ethylenedioxyphenyl | 1 |
| 394 | OH | 4-Methoxy-3-methylphenyl | 4-Methoxy-3-methylphenyl | Propyl | 5-Methoxy-3,4-methylenedioxyphenyl | 1 |
| 395 | OH | 4-Methoxy-3-methylphenyl | 4-Methoxy-3-methylphenyl | Propyl | 3,5-Diethylphenyl | 1 |
| 396 | OH | 4-Methoxy-3-methylphenyl | 4-Methoxy-3-methylphenyl | Propyl | 3,4-Dimethoxyphenyl | 1 |
| 397 | OH | 4-Methoxy-3-methylphenyl | 4-Methoxy-3-methylphenyl | Propyl | 3-Methyl-4-benzyloxyphenyl | 1 |
| 398 | OH | 4-Methoxy-3-methylphenyl | 4-Methoxy-3-methylphenyl | Propyl | 3-Benzyloxy-5-methoxyphenyl | 1 |
| 399 | OH | 4-Methoxy-3-methylphenyl | 4-Methoxy-3-methylphenyl | Propyl | 3-Benzyloxy-4-methoxyphenyl | 1 |
| 400 | OH | 4-Methoxy-3-methylphenyl | 4-Methoxy-3-methylphenyl | Propyl | 3-Hydroxy-4-methoxyphenyl | 1 |
| 401 | OH | 4-Methoxy-3-methylphenyl | 4-Methoxy-3-methylphenyl | Propyl | 4-Hydroxy-3-methoxyphenyl | 1 |
| 402 | OH | 4-Methoxy-3-methylphenyl | 4-Methoxy-3-methylphenyl | Propyl | 3,5-Bis-(trifluoromethyl)-phenyl | 1 |
| 403 | OH | 4-Methoxy-3-methylphenyl | 4-Methoxy-3-methylphenyl | Propyl | 3-Methylphenyl | 1 |
| 404 | OH | 4-Methoxy-3-methylphenyl | 4-Methoxy-3-methylphenyl | Propyl | 3-Methoxyphenyl | 1 |
| 405 | OH | 4-Methoxy-3-methylphenyl | 4-Methoxy-3-methylphenyl | Propyl | 4-Benzyloxyphenyl | 1 |
| 406 | OH | 4-Methoxy-3-methylphenyl | 4-Methoxy-3-methylphenyl | Propyl | 4-Phenoxyphenyl | 1 |
| 407 | OH | 4-Methoxy-3-methylphenyl | 4-Methoxy-3-methylphenyl | Propyl | 6-Methylpyridin-2-yl | 1 |
| 408 | OH | 4-Methoxy-3-methylphenyl | 4-Methoxy-3-methylphenyl | Propyl | 6-Ethylpyridin-2-yl | 1 |
| 409 | OH | 4-Methoxy-3-methylphenyl | 4-Methoxy-3-methylphenyl | Propyl | 6-Methoxypyridin-2-yl | 1 |
| 410 | OH | 4-Methoxy-3-methylphenyl | 4-Methoxy-3-methylphenyl | Propyl | 4,6-Dimethylpyridin-2-yl | 1 |
| 411 | OH | 4-Methoxy-3-methylphenyl | 4-Methoxy-3-methylphenyl | Propyl | 4,6-Diethylpyridin-2-yl | 1 |
| 412 | OH | 4-Methoxy-3-methylphenyl | 4-Methoxy-3-methylphenyl | Propyl | 4-Methyl-6-methoxypyridin-2-yl | 1 |
| 413 | OH | 4-Methoxy-3-methylphenyl | 4-Methoxy-3-methylphenyl | Propyl | 6,7-Dihydro-5H-cyclopenta[b]pyridin-2-yl | 1 |
| 414 | OH | 4-Methoxy-3-methylphenyl | 4-Methoxy-3-methylphenyl | Propyl | 4,6-Dimethylpyrimidin-2-yl | 1 |
| 415 | OH | 4-Methoxy-3-methylphenyl | 4-Methoxy-3-methylphenyl | Propyl | 4-Methoxy-6-methylpyrimidin-2-yl | 1 |
| 416 | OH | 4-Methoxy-3-methylphenyl | 4-Methoxy-3-methylphenyl | Propyl | 4,6-Dimethoxypyrimidin-2-yl | 1 |
| 417 | OH | 4-Methoxy-3-methylphenyl | 4-Methoxy-3-methylphenyl | Propyl | 4,6-Diethylpyrimidin-2-yl | 1 |
| 418 | OH | 4-Methoxy-3-methylphenyl | 4-Methoxy-3-methylphenyl | Propyl | 6,7-Dihydro-5H-cyclopentapyrimidin-2-yl | 1 |
| 419 | OH | 4-Methoxy-3-methylphenyl | 4-Methoxy-3-methylphenyl | Propyl | Naphth-2-yl | 1 |
| 420 | OH | 4-Methoxy-3-methylphenyl | 4-Methoxy-3-methylphenyl | Propyl | 6,7-Dihydro-5H-cyclopenta[c]pyridin-2-yl | 1 |
| 421 | OH | Phenyl | Phenyl | 2-Hydroxyethyl | Phenyl | 1 |
| 422 | OH | Phenyl | Phenyl | 2-Hydroxyethyl | 3,5-Dimethylphenyl | 1 |
| 423 | OH | Phenyl | Phenyl | 2-Hydroxyethyl | 3,5-Dimethoxyphenyl | 1 |
| 424 | OH | Phenyl | Phenyl | 2-Hydroxyethyl | 3,4-Methylenedioxyphenyl | 1 |
| 425 | OH | Phenyl | Phenyl | 2-Hydroxyethyl | 2,3-Dihydro-benzofuran-5-yl | 1 |
| 426 | OH | Phenyl | Phenyl | 2-Hydroxyethyl | 2,3-Dihydro-1H-inden-5-yl | 1 |

-continued

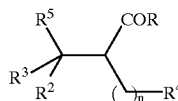

| No. | R | R² | R³ | R⁵ | R⁴ | n |
|---|---|---|---|---|---|---|
| 427 | OH | Phenyl | Phenyl | 2-Hydroxyethyl | 3-Methoxy-5-methylphenyl | 1 |
| 428 | OH | Phenyl | Phenyl | 2-Hydroxyethyl | 3,4-Ethylenedioxyphenyl | 1 |
| 429 | OH | Phenyl | Phenyl | 2-Hydroxyethyl | 5-Methoxy-3,4-methylenedioxyphenyl | 1 |
| 430 | OH | Phenyl | Phenyl | 2-Hydroxyethyl | 3,5-Diethylphenyl | 1 |
| 431 | OH | Phenyl | Phenyl | 2-Hydroxyethyl | 3,4-Dimethoxyphenyl | 1 |
| 432 | OH | Phenyl | Phenyl | 2-Hydroxyethyl | 3-Methyl-4-benzyloxyphenyl | 1 |
| 433 | OH | Phenyl | Phenyl | 2-Hydroxyethyl | 3-Benzyloxy-5-methoxyphenyl | 1 |
| 434 | OH | Phenyl | Phenyl | 2-Hydroxyethyl | 3-Benzyloxy-4-methoxyphenyl | 1 |
| 435 | OH | Phenyl | Phenyl | 2-Hydroxyethyl | 3-Hydroxy-4-methoxyphenyl | 1 |
| 436 | OH | Phenyl | Phenyl | 2-Hydroxyethyl | 4-Hydroxy-3-methoxyphenyl | 1 |
| 437 | OH | Phenyl | Phenyl | 2-Hydroxyethyl | 3,5-Bis-(trifluoromethyl)-phenyl | 1 |
| 438 | OH | Phenyl | Phenyl | 2-Hydroxyethyl | 3-Methylphenyl | 1 |
| 439 | OH | Phenyl | Phenyl | 2-Hydroxyethyl | 3-Methoxyphenyl | 1 |
| 440 | OH | Phenyl | Phenyl | 2-Hydroxyethyl | 4-Benzyloxyphenyl | 1 |
| 441 | OH | Phenyl | Phenyl | 2-Hydroxyethyl | 4-Phenoxyphenyl | 1 |
| 442 | OH | Phenyl | Phenyl | 2-Hydroxyethyl | 6-Methylpyridin-2-yl | 1 |
| 443 | OH | Phenyl | Phenyl | 2-Hydroxyethyl | 6-Ethylpyridin-2-yl | 1 |
| 444 | OH | Phenyl | Phenyl | 2-Hydroxyethyl | 6-Methoxypyridin-2-yl | 1 |
| 445 | OH | Phenyl | Phenyl | 2-Hydroxyethyl | 4,6-Dimethylpyridin-2-yl | 1 |
| 446 | OH | Phenyl | Phenyl | 2-Hydroxyethyl | 4,6-Diethylpyridin-2-yl | 1 |
| 447 | OH | Phenyl | Phenyl | 2-Hydroxyethyl | 4-Methyl-6-methoxypyridin-2-yl | 1 |
| 448 | OH | Phenyl | Phenyl | 2-Hydroxyethyl | 6,7-Dihydro-5H-cyclopenta[b]pyridin-2-yl | 1 |
| 449 | OH | Phenyl | Phenyl | 2-Hydroxyethyl | 4,6-Dimethylpyrimidin-2-yl | 1 |
| 450 | OH | Phenyl | Phenyl | 2-Hydroxyethyl | 4-Methoxy-6-methylpyrimidin-2-yl | 1 |
| 451 | OH | Phenyl | Phenyl | 2-Hydroxyethyl | 4,6-Dimethoxypyrimidin-2-yl | 1 |
| 452 | OH | Phenyl | Phenyl | 2-Hydroxyethyl | 4,6-Diethylpyrimidin-2-yl | 1 |
| 453 | OH | Phenyl | Phenyl | 2-Hydroxyethyl | 6,7-Dihydro-5H-cyclopentapyrimidin-2-yl | 1 |
| 454 | OH | Phenyl | Phenyl | 2-Hydroxyethyl | Naphth-2-yl | 1 |
| 455 | OH | Phenyl | Phenyl | 2-Hydroxyethyl | 6,7-Dihydro-5H-cyclopenta[c]pyridin-2-yl | 1 |
| 456 | OH | p-Methoxyphenyl | p-Methoxyphenyl | 2-Hydroxyethyl | Phenyl | 1 |
| 457 | OH | p-Methoxyphenyl | p-Methoxyphenyl | 2-Hydroxyethyl | 3,5-Dimethylphenyl | 1 |
| 458 | OH | p-Methoxyphenyl | p-Methoxyphenyl | 2-Hydroxyethyl | 3,5-Dimethoxyphenyl | 1 |
| 459 | OH | p-Methoxyphenyl | p-Methoxyphenyl | 2-Hydroxyethyl | 3,4-Methylenedioxyphenyl | 1 |
| 460 | OH | p-Methoxyphenyl | p-Methoxyphenyl | 2-Hydroxyethyl | 2,3-Dihydro-benzofuran-5-yl | 1 |
| 461 | OH | p-Methoxyphenyl | p-Methoxyphenyl | 2-Hydroxyethyl | 2,3-Dihydro-1H-inden-5-yl | 1 |
| 462 | OH | p-Methoxyphenyl | p-Methoxyphenyl | 2-Hydroxyethyl | 3-Methoxy-5-methylphenyl | 1 |
| 463 | OH | p-Methoxyphenyl | p-Methoxyphenyl | 2-Hydroxyethyl | 3,4-Ethylenedioxyphenyl | 1 |
| 464 | OH | p-Methoxyphenyl | p-Methoxyphenyl | 2-Hydroxyethyl | 5-Methoxy-3,4-methylenedioxyphenyl | 1 |
| 465 | OH | p-Methoxyphenyl | p-Methoxyphenyl | 2-Hydroxyethyl | 3,5-Diethylphenyl | 1 |
| 466 | OH | p-Methoxyphenyl | p-Methoxyphenyl | 2-Hydroxyethyl | 3,4-Dimethoxyphenyl | 1 |
| 467 | OH | p-Methoxyphenyl | p-Methoxyphenyl | 2-Hydroxyethyl | 3-Methyl-4-benzyloxyphenyl | 1 |
| 468 | OH | p-Methoxyphenyl | p-Methoxyphenyl | 2-Hydroxyethyl | 3-Benzyloxy-5-methoxyphenyl | 1 |
| 469 | OH | p-Methoxyphenyl | p-Methoxyphenyl | 2-Hydroxyethyl | 3-Benzyloxy-4-methoxyphenyl | 1 |
| 470 | OH | p-Methoxyphenyl | p-Methoxyphenyl | 2-Hydroxyethyl | 3-Hydroxy-4-methoxyphenyl | 1 |
| 471 | OH | p-Methoxyphenyl | p-Methoxyphenyl | 2-Hydroxyethyl | 4-Hydroxy-3-methoxyphenyl | 1 |
| 472 | OH | p-Methoxyphenyl | p-Methoxyphenyl | 2-Hydroxyethyl | 3,5-Bis-(trifluoromethyl)-phenyl | 1 |
| 473 | OH | p-Methoxyphenyl | p-Methoxyphenyl | 2-Hydroxyethyl | 3-Methylphenyl | 1 |
| 474 | OH | p-Methoxyphenyl | p-Methoxyphenyl | 2-Hydroxyethyl | 3-Methoxyphenyl | 1 |
| 475 | OH | p-Methoxyphenyl | p-Methoxyphenyl | 2-Hydroxyethyl | 4-Benzyloxyphenyl | 1 |
| 476 | OH | p-Methoxyphenyl | p-Methoxyphenyl | 2-Hydroxyethyl | 4-Phenoxyphenyl | 1 |
| 477 | OH | p-Methoxyphenyl | p-Methoxyphenyl | 2-Hydroxyethyl | 6-Methylpyridin-2-yl | 1 |
| 478 | OH | p-Methoxyphenyl | p-Methoxyphenyl | 2-Hydroxyethyl | 6-Ethylpyridin-2-yl | 1 |
| 479 | OH | p-Methoxyphenyl | p-Methoxyphenyl | 2-Hydroxyethyl | 6-Methoxypyridin-2-yl | 1 |
| 480 | OH | p-Methoxyphenyl | p-Methoxyphenyl | 2-Hydroxyethyl | 4,6-Dimethylpyridin-2-yl | 1 |
| 481 | OH | p-Methoxyphenyl | p-Methoxyphenyl | 2-Hydroxyethyl | 4,6-Diethylpyridin-2-yl | 1 |
| 482 | OH | p-Methoxyphenyl | p-Methoxyphenyl | 2-Hydroxyethyl | 4-Methyl-6-methoxypyridin-2-yl | 1 |
| 483 | OH | p-Methoxyphenyl | p-Methoxyphenyl | 2-Hydroxyethyl | 6,7-Dihydro-5H-cyclopenta[b]pyridin-2-yl | 1 |
| 484 | OH | p-Methoxyphenyl | p-Methoxyphenyl | 2-Hydroxyethyl | 4,6-Dimethylpyrimidin-2-yl | 1 |
| 485 | OH | p-Methoxyphenyl | p-Methoxyphenyl | 2-Hydroxyethyl | 4-Methoxy-6-methylpyrimidin-2-yl | 1 |
| 486 | OH | p-Methoxyphenyl | p-Methoxyphenyl | 2-Hydroxyethyl | 4,6-Dimethoxypyrimidin-2-yl | 1 |
| 487 | OH | p-Methoxyphenyl | p-Methoxyphenyl | 2-Hydroxyethyl | 4,6-Diethylpyrimidin-2-yl | 1 |
| 488 | OH | p-Methoxyphenyl | p-Methoxyphenyl | 2-Hydroxyethyl | 6,7-Dihydro-5H-cyclopentapyrimidin-2-yl | 1 |
| 489 | OH | p-Methoxyphenyl | p-Methoxyphenyl | 2-Hydroxyethyl | Naphth-2-yl | 1 |
| 490 | OH | p-Methoxyphenyl | p-Methoxyphenyl | 2-Hydroxyethyl | 6,7-Dihydro-5H-cyclopenta-[c]pyridin-2-yl | 1 |
| 491 | OH | p-Methylphenyl | p-Methylphenyl | 2-Hydroxyethyl | Phenyl | 1 |
| 492 | OH | p-Methylphenyl | p-Methylphenyl | 2-Hydroxyethyl | 3,5-Dimethylphenyl | 1 |
| 493 | OH | p-Methylphenyl | p-Methylphenyl | 2-Hydroxyethyl | 3,5-Dimethoxyphenyl | 1 |
| 494 | OH | p-Methylphenyl | p-Methylphenyl | 2-Hydroxyethyl | 3,4-Methylenedioxyphenyl | 1 |
| 495 | OH | p-Methylphenyl | p-Methylphenyl | 2-Hydroxyethyl | 2,3-Dihydro-benzofuran-5-yl | 1 |
| 496 | OH | p-Methylphenyl | p-Methylphenyl | 2-Hydroxyethyl | 2,3-Dihydro-1H-inden-5-yl | 1 |
| 497 | OH | p-Methylphenyl | p-Methylphenyl | 2-Hydroxyethyl | 3-Methoxy-5-methylphenyl | 1 |

-continued

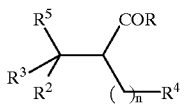

| No. | R | R² | R³ | R⁵ | R⁴ | n |
|---|---|---|---|---|---|---|
| 498 | OH | p-Methylphenyl | p-Methylphenyl | 2-Hydroxyethyl | 3,4-Ethylenedioxyphenyl | 1 |
| 499 | OH | p-Methylphenyl | p-Methylphenyl | 2-Hydroxyethyl | 5-Methoxy-3,4-methylenedioxyphenyl | 1 |
| 500 | OH | p-Methylphenyl | p-Methylphenyl | 2-Hydroxyethyl | 3,5-Diethylphenyl | 1 |
| 501 | OH | p-Methylphenyl | p-Methylphenyl | 2-Hydroxyethyl | 3,4-Dimethoxyphenyl | 1 |
| 502 | OH | p-Methylphenyl | p-Methylphenyl | 2-Hydroxyethyl | 3-Methyl-4-benzyloxyphenyl | 1 |
| 503 | OH | p-Methylphenyl | p-Methylphenyl | 2-Hydroxyethyl | 3-Benzyloxy-5-methoxyphenyl | 1 |
| 504 | OH | p-Methylphenyl | p-Methylphenyl | 2-Hydroxyethyl | 3-Benzyloxy-4-methoxyphenyl | 1 |
| 505 | OH | p-Methylphenyl | p-Methylphenyl | 2-Hydroxyethyl | 3-Hydroxy-4-methoxyphenyl | 1 |
| 506 | OH | p-Methylphenyl | p-Methylphenyl | 2-Hydroxyethyl | 4-Hydroxy-3-methoxyphenyl | 1 |
| 507 | OH | p-Methylphenyl | p-Methylphenyl | 2-Hydroxyethyl | 3,5-Bis-(trifluoromethyl)-phenyl | 1 |
| 508 | OH | p-Methylphenyl | p-Methylphenyl | 2-Hydroxyethyl | 3-Methylphenyl | 1 |
| 509 | OH | p-Methylphenyl | p-Methylphenyl | 2-Hydroxyethyl | 3-Methoxyphenyl | 1 |
| 510 | OH | p-Methylphenyl | p-Methylphenyl | 2-Hydroxyethyl | 4-Benzyloxyphenyl | 1 |
| 511 | OH | p-Methylphenyl | p-Methylphenyl | 2-Hydroxyethyl | 4-Phenoxyphenyl | 1 |
| 512 | OH | p-Methylphenyl | p-Methylphenyl | 2-Hydroxyethyl | 6-Methylpyridin-2-yl | 1 |
| 513 | OH | p-Methylphenyl | p-Methylphenyl | 2-Hydroxyethyl | 6-Ethylpyridin-2-yl | 1 |
| 514 | OH | p-Methylphenyl | p-Methylphenyl | 2-Hydroxyethyl | 6-Methoxypyridin-2-yl | 1 |
| 515 | OH | p-Methylphenyl | p-Methylphenyl | 2-Hydroxyethyl | 4,6-Dimethylpyridin-2-yl | 1 |
| 516 | OH | p-Methylphenyl | p-Methylphenyl | 2-Hydroxyethyl | 4,6-Diethylpyridin-2-yl | 1 |
| 517 | OH | p-Methylphenyl | p-Methylphenyl | 2-Hydroxyethyl | 4-Methyl-6-methoxypyridin-2-yl | 1 |
| 518 | OH | p-Methylphenyl | p-Methylphenyl | 2-Hydroxyethyl | 6,7-Dihydro-5H-cyclopenta[b]pyridin-2-yl | 1 |
| 519 | OH | p-Methylphenyl | p-Methylphenyl | 2-Hydroxyethyl | 4,6-Dimethylpyrimidin-2-yl | 1 |
| 520 | OH | p-Methylphenyl | p-Methylphenyl | 2-Hydroxyethyl | 4-Methoxy-6-methylpyrimidin-2-yl | 1 |
| 521 | OH | p-Methylphenyl | p-Methylphenyl | 2-Hydroxyethyl | 4,6-Dimethoxypyrimidin-2-yl | 1 |
| 522 | OH | p-Methylphenyl | p-Methylphenyl | 2-Hydroxyethyl | 4,6-Diethylpyrimidin-2-yl | 1 |
| 523 | OH | p-Methylphenyl | p-Methylphenyl | 2-Hydroxyethyl | 6,7-Dihydro-5H-cyclopentapyrimidin-2-yl | 1 |
| 524 | OH | p-Methylphenyl | p-Methylphenyl | 2-Hydroxyethyl | Naphth-2-yl | 1 |
| 525 | OH | p-Methylphenyl | p-Methylphenyl | 2-Hydroxyethyl | 6,7-Dihydro-5H-cyclopenta[c]pyridin-2-yl | 1 |
| 526 | OH | 4-Methoxy-3-methylphenyl | 4-Methoxy-3-methylphenyl | 2-Hydroxyethyl | Phenyl | 1 |
| 527 | OH | 4-Methoxy-3-methylphenyl | 4-Methoxy-3-methylphenyl | 2-Hydroxyethyl | 3,5-Dimethylphenyl | 1 |
| 528 | OH | 4-Methoxy-3-methylphenyl | 4-Methoxy-3-methylphenyl | 2-Hydroxyethyl | 3,5-Dimethoxyphenyl | 1 |
| 529 | OH | 4-Methoxy-3-methylphenyl | 4-Methoxy-3-methylphenyl | 2-Hydroxyethyl | 3,4-Methylenedioxyphenyl | 1 |
| 530 | OH | 4-Methoxy-3-methylphenyl | 4-Methoxy-3-methylphenyl | 2-Hydroxyethyl | 2,3-Dihydro-benzofuran-5-yl | 1 |
| 531 | OH | 4-Methoxy-3-methylphenyl | 4-Methoxy-3-methylphenyl | 2-Hydroxyethyl | 2,3-Dihydro-1H-inden-5-yl | 1 |
| 532 | OH | 4-Methoxy-3-methylphenyl | 4-Methoxy-3-methylphenyl | 2-Hydroxyethyl | 3-Methoxy-5-methylphenyl | 1 |
| 533 | OH | 4-Methoxy-3-methylphenyl | 4-Methoxy-3-methylphenyl | 2-Hydroxyethyl | 3,4-Ethylenedioxyphenyl | 1 |
| 534 | OH | 4-Methoxy-3-methylphenyl | 4-Methoxy-3-methylphenyl | 2-Hydroxyethyl | 5-Methoxy-3,4-methylenedioxyphenyl | 1 |
| 535 | OH | 4-Methoxy-3-methylphenyl | 4-Methoxy-3-methylphenyl | 2-Hydroxyethyl | 3,5-Diethylphenyl | 1 |
| 536 | OH | 4-Methoxy-3-methylphenyl | 4-Methoxy-3-methylphenyl | 2-Hydroxyethyl | 3,4-Dimethoxyphenyl | 1 |
| 537 | OH | 4-Methoxy-3-methylphenyl | 4-Methoxy-3-methylphenyl | 2-Hydroxyethyl | 3-Methyl-4-benzyloxyphenyl | 1 |
| 538 | OH | 4-Methoxy-3-methylphenyl | 4-Methoxy-3-methylphenyl | 2-Hydroxyethyl | 3-Benzyloxy-5-methoxyphenyl | 1 |
| 539 | OH | 4-Methoxy-3-methylphenyl | 4-Methoxy-3-methylphenyl | 2-Hydroxyethyl | 3-Benzyloxy-4-methoxyphenyl | 1 |
| 540 | OH | 4-Methoxy-3-methylphenyl | 4-Methoxy-3-methylphenyl | 2-Hydroxyethyl | 3-Hydroxy-4-methoxyphenyl | 1 |
| 541 | OH | 4-Methoxy-3-methylphenyl | 4-Methoxy-3-methylphenyl | 2-Hydroxyethyl | 4-Hydroxy-3-methoxyphenyl | 1 |
| 542 | OH | 4-Methoxy-3-methylphenyl | 4-Methoxy-3-methylphenyl | 2-Hydroxyethyl | 3,5-Bis-(trifluoromethyl)-phenyl | 1 |
| 543 | OH | 4-Methoxy-3-methylphenyl | 4-Methoxy-3-methylphenyl | 2-Hydroxyethyl | 3-Methylphenyl | 1 |
| 544 | OH | 4-Methoxy-3-methylphenyl | 4-Methoxy-3-methylphenyl | 2-Hydroxyethyl | 3-Methoxyphenyl | 1 |
| 545 | OH | 4-Methoxy-3-methylphenyl | 4-Methoxy-3-methylphenyl | 2-Hydroxyethyl | 4-Benzyloxyphenyl | 1 |
| 546 | OH | 4-Methoxy-3-methylphenyl | 4-Methoxy-3-methylphenyl | 2-Hydroxyethyl | 4-Phenoxyphenyl | 1 |
| 547 | OH | 4-Methoxy-3-methylphenyl | 4-Methoxy-3-methylphenyl | 2-Hydroxyethyl | 6-Methylpyridin-2-yl | 1 |
| 548 | OH | 4-Methoxy-3-methylphenyl | 4-Methoxy-3-methylphenyl | 2-Hydroxyethyl | 6-Ethylpyridin-2-yl | 1 |
| 549 | OH | 4-Methoxy-3-methylphenyl | 4-Methoxy-3-methylphenyl | 2-Hydroxyethyl | 6-Methoxypyridin-2-yl | 1 |
| 550 | OH | 4-Methoxy-3-methylphenyl | 4-Methoxy-3-methylphenyl | 2-Hydroxyethyl | 4,6-Dimethylpyridin-2-yl | 1 |
| 551 | OH | 4-Methoxy-3-methylphenyl | 4-Methoxy-3-methylphenyl | 2-Hydroxyethyl | 4,6-Diethylpyridin-2-yl | 1 |
| 552 | OH | 4-Methoxy-3-methylphenyl | 4-Methoxy-3-methylphenyl | 2-Hydroxyethyl | 4-Methyl-6-methoxypyridin-2-yl | 1 |
| 553 | OH | 4-Methoxy-3-methylphenyl | 4-Methoxy-3-methylphenyl | 2-Hydroxyethyl | 6,7-Dihydro-5H-cyclopenta[b]pyridin-2-yl | 1 |
| 554 | OH | 4-Methoxy-3-methylphenyl | 4-Methoxy-3-methylphenyl | 2-Hydroxyethyl | 4,6-Dimethylpyrimidin-2-yl | 1 |
| 555 | OH | 4-Methoxy-3-methylphenyl | 4-Methoxy-3-methylphenyl | 2-Hydroxyethyl | 4-Methoxy-6-methylpyrimidin-2-yl | 1 |
| 556 | OH | 4-Methoxy-3-methylphenyl | 4-Methoxy-3-methylphenyl | 2-Hydroxyethyl | 4,6-Dimethoxypyrimidin-2-yl | 1 |
| 557 | OH | 4-Methoxy-3-methylphenyl | 4-Methoxy-3-methylphenyl | 2-Hydroxyethyl | 4,6-Diethylpyrimidin-2-yl | 1 |
| 558 | OH | 4-Methoxy-3-methylphenyl | 4-Methoxy-3-methylphenyl | 2-Hydroxyethyl | 6,7-Dihydro-5H-cyclopentapyrimidin-2-yl | 1 |
| 559 | OH | 4-Methoxy-3-methylphenyl | 4-Methoxy-3-methylphenyl | 2-Hydroxyethyl | Naphth-2-yl | 1 |
| 560 | OH | 4-Methoxy-3-methylphenyl | 4-Methoxy-3-methylphenyl | 2-Hydroxyethyl | 6,7-Dihydro-5H-cyclopenta[c]pyridin-2-yl | 1 |
| 561 | OH | Phenyl | Phenyl | 2-Methylethyl | Phenyl | 1 |
| 562 | OH | Phenyl | Phenyl | 2-Methylethyl | 3,5-Dimethylphenyl | 1 |
| 563 | OH | Phenyl | Phenyl | 2-Methylethyl | 3,5-Dimethoxyphenyl | 1 |
| 564 | OH | Phenyl | Phenyl | 2-Methylethyl | 3,4-Methylenedioxyphenyl | 1 |
| 565 | OH | Phenyl | Phenyl | 2-Methylethyl | 2,3-Dihydro-benzofuran-5-yl | 1 |
| 566 | OH | Phenyl | Phenyl | 2-Methylethyl | 2,3-Dihydro-1H-inden-5-yl | 1 |
| 567 | OH | Phenyl | Phenyl | 2-Methylethyl | 3-Methoxy-5-methylphenyl | 1 |
| 568 | OH | Phenyl | Phenyl | 2-Methylethyl | 3,4-Ethylenedioxyphenyl | 1 |

-continued

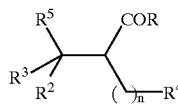

| No. | R | R² | R³ | R⁵ | R⁴ | n |
|---|---|---|---|---|---|---|
| 569 | OH | Phenyl | Phenyl | 2-Methylethyl | 5-Methoxy-3,4-methylenedioxyphenyl | 1 |
| 570 | OH | Phenyl | Phenyl | 2-Methylethyl | 3,5-Diethylphenyl | 1 |
| 571 | OH | Phenyl | Phenyl | 2-Methylethyl | 3,4-Dimethoxyphenyl | 1 |
| 572 | OH | Phenyl | Phenyl | 2-Methylethyl | 3-Methyl-4-benzyloxyphenyl | 1 |
| 573 | OH | Phenyl | Phenyl | 2-Methylethyl | 3-Benzyloxy-5-methoxyphenyl | 1 |
| 574 | OH | Phenyl | Phenyl | 2-Methylethyl | 3-Benzyloxy-4-methoxyphenyl | 1 |
| 575 | OH | Phenyl | Phenyl | 2-Methylethyl | 3-Hydroxy-4-methoxyphenyl | 1 |
| 576 | OH | Phenyl | Phenyl | 2-Methylethyl | 4-Hydroxy-3-methoxyphenyl | 1 |
| 577 | OH | Phenyl | Phenyl | 2-Methylethyl | 3,5-Bis-(trifluoromethyl)-phenyl | 1 |
| 578 | OH | Phenyl | Phenyl | 2-Methylethyl | 3-Methylphenyl | 1 |
| 579 | OH | Phenyl | Phenyl | 2-Methylethyl | 3-Methoxyphenyl | 1 |
| 580 | OH | Phenyl | Phenyl | 2-Methylethyl | 4-Benzyloxyphenyl | 1 |
| 581 | OH | Phenyl | Phenyl | 2-Methylethyl | 4-Phenoxyphenyl | 1 |
| 582 | OH | Phenyl | Phenyl | 2-Methylethyl | 6-Methylpyridin-2-yl | 1 |
| 583 | OH | Phenyl | Phenyl | 2-Methylethyl | 6-Ethylpyridin-2-yl | 1 |
| 584 | OH | Phenyl | Phenyl | 2-Methylethyl | 6-Methoxypyridin-2-yl | 1 |
| 585 | OH | Phenyl | Phenyl | 2-Methylethyl | 4,6-Dimethylpyridin-2-yl | 1 |
| 586 | OH | Phenyl | Phenyl | 2-Methylethyl | 4,6-Diethylpyridin-2-yl | 1 |
| 587 | OH | Phenyl | Phenyl | 2-Methylethyl | 4-Methyl-6-methoxypyridin-2-yl | 1 |
| 588 | OH | Phenyl | Phenyl | 2-Methylethyl | 6,7-Dihydro-5H-cyclopenta[b]pyridin-2-yl | 1 |
| 589 | OH | Phenyl | Phenyl | 2-Methylethyl | 4,6-Dimethylpyrimidin-2-yl | 1 |
| 590 | OH | Phenyl | Phenyl | 2-Methylethyl | 4-Methoxy-6-methylpyrimidin-2-yl | 1 |
| 591 | OH | Phenyl | Phenyl | 2-Methylethyl | 4,6-Dimethoxypyrimidin-2-yl | 1 |
| 592 | OH | Phenyl | Phenyl | 2-Methylethyl | 4,6-Diethylpyrimidin-2-yl | 1 |
| 593 | OH | Phenyl | Phenyl | 2-Methylethyl | 6,7-Dihydro-5H-cyclopentapyrimidin-2-yl | 1 |
| 594 | OH | Phenyl | Phenyl | 2-Methylethyl | Naphth-2-yl | 1 |
| 595 | OH | Phenyl | Phenyl | 2-Methylethyl | 6,7-Dihydro-5H-cyclopenta[c]pyridin-2-yl | 1 |
| 596 | OH | p-Methoxyphenyl | p-Methoxyphenyl | 2-Methylethyl | Phenyl | 1 |
| 597 | OH | p-Methoxyphenyl | p-Methoxyphenyl | 2-Methylethyl | 3,5-Dimethylphenyl | 1 |
| 598 | OH | p-Methoxyphenyl | p-Methoxyphenyl | 2-Methylethyl | 3,5-Dimethoxyphenyl | 1 |
| 599 | OH | p-Methoxyphenyl | p-Methoxyphenyl | 2-Methylethyl | 3,4-Methylenedioxyphenyl | 1 |
| 600 | OH | p-Methoxyphenyl | p-Methoxyphenyl | 2-Methylethyl | 2,3-Dihydro-benzofuran-5-yl | 1 |
| 601 | OH | p-Methoxyphenyl | p-Methoxyphenyl | 2-Methylethyl | 2,3-Dihydro-1H-inden-5-yl | 1 |
| 602 | OH | p-Methoxyphenyl | p-Methoxyphenyl | 2-Methylethyl | 3-Methoxy-5-methylphenyl | 1 |
| 603 | OH | p-Methoxyphenyl | p-Methoxyphenyl | 2-Methylethyl | 3,4-Ethylenedioxyphenyl | 1 |
| 604 | OH | p-Methoxyphenyl | p-Methoxyphenyl | 2-Methylethyl | 5-Methoxy-3,4-methylenedioxyphenyl | 1 |
| 605 | OH | p-Methoxyphenyl | p-Methoxyphenyl | 2-Methylethyl | 3,5-Diethylphenyl | 1 |
| 606 | OH | p-Methoxyphenyl | p-Methoxyphenyl | 2-Methylethyl | 3,4-Dimethoxyphenyl | 1 |
| 607 | OH | p-Methoxyphenyl | p-Methoxyphenyl | 2-Methylethyl | 3-Methyl-4-benzyloxyphenyl | 1 |
| 608 | OH | p-Methoxyphenyl | p-Methoxyphenyl | 2-Methylethyl | 3-Benzyloxy-5-methoxyphenyl | 1 |
| 609 | OH | p-Methoxyphenyl | p-Methoxyphenyl | 2-Methylethyl | 3-Benzyloxy-4-methoxyphenyl | 1 |
| 610 | OH | p-Methoxyphenyl | p-Methoxyphenyl | 2-Methylethyl | 3-Hydroxy-4-methoxyphenyl | 1 |
| 611 | OH | p-Methoxyphenyl | p-Methoxyphenyl | 2-Methylethyl | 4-Hydroxy-3-methoxyphenyl | 1 |
| 612 | OH | p-Methoxyphenyl | p-Methoxyphenyl | 2-Methylethyl | 3,5-Bis-(trifluoromethyl)-phenyl | 1 |
| 613 | OH | p-Methoxyphenyl | p-Methoxyphenyl | 2-Methylethyl | 3-Methylphenyl | 1 |
| 614 | OH | p-Methoxyphenyl | p-Methoxyphenyl | 2-Methylethyl | 3-Methoxyphenyl | 1 |
| 615 | OH | p-Methoxyphenyl | p-Methoxyphenyl | 2-Methylethyl | 4-Benzyloxyphenyl | 1 |
| 616 | OH | p-Methoxyphenyl | p-Methoxyphenyl | 2-Methylethyl | 4-Phenoxyphenyl | 1 |
| 617 | OH | p-Methoxyphenyl | p-Methoxyphenyl | 2-Methylethyl | 6-Methylpyridin-2-yl | 1 |
| 618 | OH | p-Methoxyphenyl | p-Methoxyphenyl | 2-Methylethyl | 6-Ethylpyridin-2-yl | 1 |
| 619 | OH | p-Methoxyphenyl | p-Methoxyphenyl | 2-Methylethyl | 6-Methoxypyridin-2-yl | 1 |
| 620 | OH | p-Methoxyphenyl | p-Methoxyphenyl | 2-Methylethyl | 4,6-Dimethylpyridin-2-yl | 1 |
| 621 | OH | p-Methoxyphenyl | p-Methoxyphenyl | 2-Methylethyl | 4,6-Diethylpyridin-2-yl | 1 |
| 622 | OH | p-Methoxyphenyl | p-Methoxyphenyl | 2-Methylethyl | 4-Methyl-6-methoxypyridin-2-yl | 1 |
| 623 | OH | p-Methoxyphenyl | p-Methoxyphenyl | 2-Methylethyl | 6,7-Dihydro-5H-cyclopenta[b]pyridin-2-yl | 1 |
| 624 | OH | p-Methoxyphenyl | p-Methoxyphenyl | 2-Methylethyl | 4,6-Dimethylpyrimidin-2-yl | 1 |
| 625 | OH | p-Methoxyphenyl | p-Methoxyphenyl | 2-Methylethyl | 4-Methoxy-6-methylpyrimidin-2-yl | 1 |
| 626 | OH | p-Methoxyphenyl | p-Methoxyphenyl | 2-Methylethyl | 4,6-Dimethoxypyrimidin-2-yl | 1 |
| 627 | OH | p-Methoxyphenyl | p-Methoxyphenyl | 2-Methylethyl | 4,6-Diethylpyrimidin-2-yl | 1 |
| 628 | OH | p-Methoxyphenyl | p-Methoxyphenyl | 2-Methylethyl | 6,7-Dihydro-5H-cyclopentapyrimidin-2-yl | 1 |
| 629 | OH | p-Methoxyphenyl | p-Methoxyphenyl | 2-Methylethyl | Naphth-2-yl | 1 |
| 630 | OH | p-Methoxyphenyl | p-Methoxyphenyl | 2-Methylethyl | 6,7-Dihydro-5H-cyclopenta[c]pyridin-2-yl | 1 |
| 631 | OH | p-Methylphenyl | p-Methylphenyl | 2-Methylethyl | Phenyl | 1 |
| 632 | OH | p-Methylphenyl | p-Methylphenyl | 2-Methylethyl | 3,5-Dimethylphenyl | 1 |
| 633 | OH | p-Methylphenyl | p-Methylphenyl | 2-Methylethyl | 3,5-Dimethoxyphenyl | 1 |
| 634 | OH | p-Methylphenyl | p-Methylphenyl | 2-Methylethyl | 3,4-Methylenedioxyphenyl | 1 |
| 635 | OH | p-Methylphenyl | p-Methylphenyl | 2-Methylethyl | 2,3-Dihydro-benzofuran-5-yl | 1 |
| 636 | OH | p-Methylphenyl | p-Methylphenyl | 2-Methylethyl | 2,3-Dihydro-1H-inden-5-yl | 1 |
| 637 | OH | p-Methylphenyl | p-Methylphenyl | 2-Methylethyl | 3-Methoxy-5-methylphenyl | 1 |
| 638 | OH | p-Methylphenyl | p-Methylphenyl | 2-Methylethyl | 3,4-Ethylenedioxyphenyl | 1 |
| 639 | OH | p-Methylphenyl | p-Methylphenyl | 2-Methylethyl | 5-Methoxy-3,4-methylenedioxyphenyl | 1 |

-continued

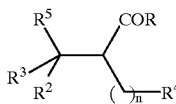

| No. | R | R² | R³ | R⁵ | R⁴ | n |
|---|---|---|---|---|---|---|
| 640 | OH | p-Methylphenyl | p-Methylphenyl | 2-Methylethyl | 3,5-Diethylphenyl | 1 |
| 641 | OH | p-Methylphenyl | p-Methylphenyl | 2-Methylethyl | 3,4-Dimethoxyphenyl | 1 |
| 642 | OH | p-Methylphenyl | p-Methylphenyl | 2-Methylethyl | 3-Methyl-4-benzyloxyphenyl | 1 |
| 643 | OH | p-Methylphenyl | p-Methylphenyl | 2-Methylethyl | 3-Benzyloxy-5-methoxyphenyl | 1 |
| 644 | OH | p-Methylphenyl | p-Methylphenyl | 2-Methylethyl | 3-Benzyloxy-4-methoxyphenyl | 1 |
| 645 | OH | p-Methylphenyl | p-Methylphenyl | 2-Methylethyl | 3-Hydroxy-4-methoxyphenyl | 1 |
| 646 | OH | p-Methylphenyl | p-Methylphenyl | 2-Methylethyl | 4-Hydroxy-3-methoxyphenyl | 1 |
| 647 | OH | p-Methylphenyl | p-Methylphenyl | 2-Methylethyl | 3,5-Bis-(trifluoromethyl)-phenyl | 1 |
| 648 | OH | p-Methylphenyl | p-Methylphenyl | 2-Methylethyl | 3,5-Bis-(trifluoromethyl)-phenyl | 1 |
| 649 | OH | p-Methylphenyl | p-Methylphenyl | 2-Methylethyl | 3-Methoxyphenyl | 1 |
| 650 | OH | p-Methylphenyl | p-Methylphenyl | 2-Methylethyl | 4-Benzyloxyphenyl | 1 |
| 651 | OH | p-Methylphenyl | p-Methylphenyl | 2-Methylethyl | 4-Phenoxyphenyl | 1 |
| 652 | OH | p-Methylphenyl | p-Methylphenyl | 2-Methylethyl | 6-Methylpyridin-2-yl | 1 |
| 653 | OH | p-Methylphenyl | p-Methylphenyl | 2-Methylethyl | 6-Ethylpyridin-2-yl | 1 |
| 654 | OH | p-Methylphenyl | p-Methylphenyl | 2-Methylethyl | 6-Methoxypyridin-2-yl | 1 |
| 655 | OH | p-Methylphenyl | p-Methylphenyl | 2-Methylethyl | 4,6-Dimethylpyridin-2-yl | 1 |
| 656 | OH | p-Methylphenyl | p-Methylphenyl | 2-Methylethyl | 4,6-Diethylpyridin-2-yl | 1 |
| 657 | OH | p-Methylphenyl | p-Methylphenyl | 2-Methylethyl | 4-Methyl-6-methoxypyridin-2-yl | 1 |
| 658 | OH | p-Methylphenyl | p-Methylphenyl | 2-Methylethyl | 6,7-Dihydro-5H-cyclopenta[b]pyridin-2-yl | 1 |
| 659 | OH | p-Methylphenyl | p-Methylphenyl | 2-Methylethyl | 4,6-Dimethylpyrimidin-2-yl | 1 |
| 660 | OH | p-Methylphenyl | p-Methylphenyl | 2-Methylethyl | 4-Methoxy-6-methylpyrimidin-2-yl | 1 |
| 661 | OH | p-Methylphenyl | p-Methylphenyl | 2-Methylethyl | 4,6-Dimethoxypyrimidin-2-yl | 1 |
| 662 | OH | p-Methylphenyl | p-Methylphenyl | 2-Methylethyl | 4,6-Diethylpyrimidin-2-yl | 1 |
| 663 | OH | p-Methylphenyl | p-Methylphenyl | 2-Methylethyl | 6,7-Dihydro-5H-cyclopentapyrimidin-2-yl | 1 |
| 664 | OH | p-Methylphenyl | p-Methylphenyl | 2-Methylethyl | Naphth-2-yl | 1 |
| 665 | OH | p-Methylphenyl | p-Methylphenyl | 2-Methylethyl | 6,7-Dihydro-5H-cyclopenta[c]pyridin-2-yl | 1 |
| 666 | OH | 4-Methoxy-3-methylphenyl | 4-Methoxy-3-methylphenyl | 2-Methylethyl | Phenyl | 1 |
| 667 | OH | 4-Methoxy-3-methylphenyl | 4-Methoxy-3-methylphenyl | 2-Methylethyl | 3,5-Dimethylphenyl | 1 |
| 668 | OH | 4-Methoxy-3-methylphenyl | 4-Methoxy-3-methylphenyl | 2-Methylethyl | 3,5-Dimethoxyphenyl | 1 |
| 669 | OH | 4-Methoxy-3-methylphenyl | 4-Methoxy-3-methylphenyl | 2-Methylethyl | 3,4-Methylenedioxyphenyl | 1 |
| 670 | OH | 4-Methoxy-3-methylphenyl | 4-Methoxy-3-methylphenyl | 2-Methylethyl | 2,3-Dihydro-benzofuran-5-yl | 1 |
| 671 | OH | 4-Methoxy-3-methylphenyl | 4-Methoxy-3-methylphenyl | 2-Methylethyl | 2,3-Dihydro-1H-inden-5-yl | 1 |
| 672 | OH | 4-Methoxy-3-methylphenyl | 4-Methoxy-3-methylphenyl | 2-Methylethyl | 3-Methoxy-5-methylphenyl | 1 |
| 673 | OH | 4-Methoxy-3-methylphenyl | 4-Methoxy-3-methylphenyl | 2-Methylethyl | 3,4-Ethylenedioxyphenyl | 1 |
| 674 | OH | 4-Methoxy-3-methylphenyl | 4-Methoxy-3-methylphenyl | 2-Methylethyl | 5-Methoxy-3,4-methylenedioxyphenyl | 1 |
| 675 | OH | 4-Methoxy-3-methylphenyl | 4-Methoxy-3-methylphenyl | 2-Methylethyl | 3,5-Diethylphenyl | 1 |
| 676 | OH | 4-Methoxy-3-methylphenyl | 4-Methoxy-3-methylphenyl | 2-Methylethyl | 3,4-Dimethoxyphenyl | 1 |
| 677 | OH | 4-Methoxy-3-methylphenyl | 4-Methoxy-3-methylphenyl | 2-Methylethyl | 3-Methyl-4-benzyloxyphenyl | 1 |
| 678 | OH | 4-Methoxy-3-methylphenyl | 4-Methoxy-3-methylphenyl | 2-Methylethyl | 3-Benzyloxy-5-methoxyphenyl | 1 |
| 679 | OH | 4-Methoxy-3-methylphenyl | 4-Methoxy-3-methylphenyl | 2-Methylethyl | 3-Benzyloxy-4-methoxyphenyl | 1 |
| 680 | OH | 4-Methoxy-3-methylphenyl | 4-Methoxy-3-methylphenyl | 2-Methylethyl | 3-Hydroxy-4-methoxyphenyl | 1 |
| 681 | OH | 4-Methoxy-3-methylphenyl | 4-Methoxy-3-methylphenyl | 2-Methylethyl | 4-Hydroxy-3-methoxyphenyl | 1 |
| 682 | OH | 4-Methoxy-3-methylphenyl | 4-Methoxy-3-methylphenyl | 2-Methylethyl | 3,5-Bis-(trifluoromethyl)-phenyl | 1 |
| 683 | OH | 4-Methoxy-3-methylphenyl | 4-Methoxy-3-methylphenyl | 2-Methylethyl | 3-Methylphenyl | 1 |
| 684 | OH | 4-Methoxy-3-methylphenyl | 4-Methoxy-3-methylphenyl | 2-Methylethyl | 3-Methoxyphenyl | 1 |
| 685 | OH | 4-Methoxy-3-methylphenyl | 4-Methoxy-3-methylphenyl | 2-Methylethyl | 4-Benzyloxyphenyl | 1 |
| 686 | OH | 4-Methoxy-3-methylphenyl | 4-Methoxy-3-methylphenyl | 2-Methylethyl | 4-Phenoxyphenyl | 1 |
| 687 | OH | 4-Methoxy-3-methylphenyl | 4-Methoxy-3-methylphenyl | 2-Methylethyl | 6-Methylpyridin-2-yl | 1 |
| 688 | OH | 4-Methoxy-3-methylphenyl | 4-Methoxy-3-methylphenyl | 2-Methylethyl | 6-Ethylpyridin-2-yl | 1 |
| 689 | OH | 4-Methoxy-3-methylphenyl | 4-Methoxy-3-methylphenyl | 2-Methylethyl | 6-Methoxypyridin-2-yl | 1 |
| 690 | OH | 4-Methoxy-3-methylphenyl | 4-Methoxy-3-methylphenyl | 2-Methylethyl | 4,6-Dimethylpyridin-2-yl | 1 |
| 691 | OH | 4-Methoxy-3-methylphenyl | 4-Methoxy-3-methylphenyl | 2-Methylethyl | 4,6-Diethylpyridin-2-yl | 1 |
| 692 | OH | 4-Methoxy-3-methylphenyl | 4-Methoxy-3-methylphenyl | 2-Methylethyl | 4-Methyl-6-methoxypyridin-2-yl | 1 |
| 693 | OH | 4-Methoxy-3-methylphenyl | 4-Methoxy-3-methylphenyl | 2-Methylethyl | 6,7-Dihydro-5H-cyclopenta[b]pyridin-2-yl | 1 |
| 694 | OH | 4-Methoxy-3-methylphenyl | 4-Methoxy-3-methylphenyl | 2-Methylethyl | 4,6-Dimethylpyrimidin-2-yl | 1 |
| 695 | OH | 4-Methoxy-3-methylphenyl | 4-Methoxy-3-methylphenyl | 2-Methylethyl | 4-Methoxy-6-methylpyrimidin-2-yl | 1 |
| 696 | OH | 4-Methoxy-3-methylphenyl | 4-Methoxy-3-methylphenyl | 2-Methylethyl | 4,6-Dimethoxypyrimidin-2-yl | 1 |
| 697 | OH | 4-Methoxy-3-methylphenyl | 4-Methoxy-3-methylphenyl | 2-Methylethyl | 4,6-Diethylpyrimidin-2-yl | 1 |
| 698 | OH | 4-Methoxy-3-methylphenyl | 4-Methoxy-3-methylphenyl | 2-Methylethyl | 6,7-Dihydro-5H-cyclopentapyrimidin-2-yl | 1 |
| 699 | OH | 4-Methoxy-3-methylphenyl | 4-Methoxy-3-methylphenyl | 2-Methylethyl | Naphth-2-yl | 1 |
| 700 | OH | 4-Methoxy-3-methylphenyl | 4-Methoxy-3-methylphenyl | 2-Methylethyl | 6,7-Dihydro-5H-cyclopenta[c]pyridin-2-yl | 1 |

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, kidney failure caused by ischemia and by intoxication, and hypertension.

The good effect of the compounds can be shown in the following tests:

Receptor-Binding Studies

Cloned human $ET_A$ receptor-expressing CHO cells and guinea pig cerebellar membranes with >60% ETB receptors by comparison with $ET_A$ receptors were employed for binding studies.

Membrane Preparation

The $ET_A$ receptor-expressing CHO cells were grown in $F_{12}$ medium containing 10% fetal calf serum, 1% glutamine, 100 U/ml penicillin and 0.2% streptomycin (Gibco BRL, Gaithersburg, Md., USA). After 48 h, the cells were washed with PBS and incubated with 0.05% trypsin-containing PBS for 5 min. Then neutralization was carried out with $F_{12}$ medium, and the cells were collected by centrifugation at 300×g. To lyse the cells, the pellet was briefly washed with lysis buffer (5 mM tris-HCl, pH 7.4 with 10% glycerol) and then incubated at a concentration of $10^7$ cells/ml of lysis buffer at 4°-C. for 30 min. The membranes were centrifuged at 20,000×g for 10 min, and the pellet was stored in liquid nitrogen.

Guinea pig cerebella were homogenized in a Potter-Elvejhem homogenizer and obtained by differential centrifugation at 1,000×g for 10 min and repeated centrifugation of the supernatant at 20,000×g for 10 min.

Binding Assays

For the $ET_A$ and $ET_B$ receptor binding assay, the membranes were suspended in an incubation buffer (50 mM tris-HCl, pH 7.4, with 5 mM $MnCl_2$, 40 µg/ml bacitracin and 0.2% BSA) at a concentration of 50 µg of protein per assay mixture and incubated in the presence and absence of test substance with 25 pM $^{125}I$-$ET_1$ ($ET_A$ receptor assay) or 25 pM $^{125}$-$RZ_3$ (ETB receptor assay) at 25° C. The nonspecific binding was determined with $10^{-7}$ M $ET_1$. After 30 min, the free and bound radioligand were separated by filtration through GF/B glass fiber filters (Whatman, England) on a Skatron cell collector (Skatron, Lier, Norway), and the filters were washed with ice-cold tris-HCl buffer, pH 7.4 with 0.2% BSA. The radioactivity collected on the filters was quantified using a Packard 2200 CA liquid scintillation counter.

Functional in vitro assay system for searching for endothelin receptor (subtype A) antagonists This assay system is a functional, cell-based assay for endothelin receptors. Certain cells show, when they are stimulated with endothelin 1 (ET1), an increase in the intracellular calcium concentration. This increase can be measured in intact cells which have been loaded with calcium-sensitive dyes.

1-Fibroblasts which were isolated from rats and in which an endogenous endothelin receptor of the A subtype had been detected were loaded with the fluorescent dye Fura 2-an as follows: after tripysinization, the cells were resuspended in buffer A (120 mM NaCl, 5 mM KCL, 1.5 mM $MgCl_2$, 1 mM $CaCl_2$, 25 mM HEPES, 10 mM Glucose, pH 7.4) to a density of $2\times10^6$/ml and incubated with Fura-2-am (2 µM), Pluronic F-127 (0.04%) and DMSO (0.2%) at 37° C. in the dark for 30 min. The cells were then washed twice with buffer A and resuspended at $2\times10^6$/ml.

The fluorescence signal from $2\times10^5$ cells per ml with Ex/Em 380/510 was recorded continuously at 30° C. The test substances and, after an incubation time of 3 min, ET1 were added to the cells. The maximum change in the fluorescence was determined over 30 min. The response of the cells to ET1 without previous addition of a test substance served as control and was set equal to 100%.

In Vivo Testing of ET Antagonists

Male SD rats weighting 250–300 g were anesthetized with amobarbital, artificially ventilated, vagotomized and pithed. The carotid artery and the jugular vein were catheterized.

Intravenous administration of 1 µg/kg ET1 to control animals leads to a distinct rise in blood pressure which persists for a lengthy period.

The test compounds was [sic] injected i.v. (1 ml/kg) into the test animals 5 or 30 min before ET1 administration. To determine the ET-antagonistic properties, the increase in blood pressure in the test animals was compared with that in the control animals.

Endothelin-1 Induced Sudden Death in Mice

The principle of the test comprises the inhibition of the sudden heart death in mice which is caused by endothelin, probably due to constriction of the coronary vessels, by pretreatment with endothelin receptor antagonists. Intravenous injection of 10 nmol/kg endothelin in a volume of 5 ml/kg of body weight results in death of the animals within a few minutes.

The lethal endothelin-1 dose is checked in each case on a small group of animals. If the test substance is administered intravenously, it is usually followed after 5 min by the endothelin-1 injection which was lethal in the reference group. With other modes of administration, the times before administration are longer, where appropriate up to several hours.

The survival rate is recorded and effective doses which protect 50% of the animals for 24 h or longer against endothelin-induced heart death (ED 50) are determined.

Functional Test for Endothelin Receptor Antagonists on Vessels

Segments of rabbit aorta with an initial tension of 2 g and a relaxation time of 1 h in Krebs-Henseleit solution at 37° C. and at a pH of from 7.3 to 7.4 are initially induced to contract with $K^+$. After washing out, an endothelin dose-effect plot is constructed up to the maximum.

Potential endothelin antagonists are administered to other preparations of the same vessel 15 min before starting the endothelin dose-effect plot. The effects of endothelin are calculated as a % of the $K^+$ contraction. Effective endothelin antagonists result in a shift in the endothelin dose-effect plot to the right.

The compounds according to the invention can be administered orally or parenterally (subcutaneously, intravenously, intramuscularly, intraperitoneally) in a conventional way. Administration can also take place with vapors or sprays through the nasopharyngeal space.

The dosage depends on the age, condition and weight of the patient and on the mode of administration. As a rule, the daily dose of agent is about 0.5–50 mg/kg of body weight on oral administration and about 0.1–10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The agents can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of the agent.

Synthetic Examples

Example 1

3,3-Bis(4-methoxyphenyl)butanoic acid a) Ethyl (2E,Z)-3-(4-methoxyphenyl)-2-butenoate (6.6 g, 30 mmol) were dissolved in anisole (4.9 g, 45 mmol) at 0°

C., and 50 ml of 80% $H_2SO_4$ were cautiously added. The 2-phase mixture was vigorously stirred at room temperature for 20 h and then poured onto ice, and the product was extracted with ethyl acetate. The organic phase was dried ($Na_2SO_4$), filtered and concentrated, the residue was taken up with ether and extracted with 2N sodium hydroxide solution, and the ether phase was discarded. The alkaline phase was adjusted to pH 2 with 2N HCl, and the product was extracted with ethyl acetate. The organic phase was then dried ($Na_2SO_4$), filtered and concentrated, and the solid residue was stirred with diisopropyl ether. The product was filtered off with suction and dried. 5.1 g of a white powder (56%) remained.

Melting point: 161–164° C.

Further working up of the mother liquor was possible, resulting in a further 1.1 g (12%) of the acid.

The acid can also be prepared by the following alternative:

b) At 0° C., 32 ml of anisole (294 mmol) were mixed with 33 ml of ethyl acetoacetate (258 mmol), 150 ml of 70% $H_2SO_4$ were cautiously added, and the resulting 2-phase mixture was vigorously stirred at room temperature for 72 h. The mixture was then poured onto ice and worked up further as under 1a). The residue was recrystallized from diisopropyl ether. 15.3 g (35%) of white solid remained.

c) Similar to the preparation of 3,3-diphenylbutanoic acid (Examples 3, 4)

Example 2

(2R, S)-3,3-Bis-(4-methoxyphenyl)-2-(3', 4'-methylenedioxybenzyl)-butanoic acid

Butyllithium (13.8 ml, 22 mmol, 1.6M in hexane) was added to a solution of diisopropylamine (3.1 ml, 22 mmol) in 50 ml of dry tetrahydrofuran under nitrogen at –10° C., the mixture was stirred at –10° C. for 5 min and then, at 0° C., 3,3-bis(4-methoxyphenyl)butanoic acid (3.0 g, 10 mmol) in 15 ml of absolute THF was added dropwise. After the addition was complete, the mixture was stirred at room temperature for 1 h, cooled to –20° C, and, after addition of piperonyl bromide (2.6 g, 12 mmol) in 10 ml of THF, stirred at room temperature for 72 h. The mixture was then quenched with saturated $NH_4Cl$ solution, the organic phase was separated off and the aqueous was extracted with ethyl acetate. The combined organic extracts were dried ($Na_2SO_4$), filtered and concentrated in a rotary evaporator. The brown residue was chromatographed on silica gel (methanol/$CH_2Cl_2$ 1:19), resulting in 1.3 g (30%) of product as a white foam.

Melting point: 137–140° C. (from diisopropyl ether)

Example 3

Ethyl 3,3-diphenylbutanoate

At 0° C., 65 g of $AlCl_3$ (487 mmol) were suspended in 500 ml of benzene, and 61.7 g of ethyl (2E,Z)-3-phenyl-2-butenoate were slowly added. The dark red solution was stirred at room temperature for 20 h and then poured into a mixture of ice and concentrated HCl. The organic phase was separated off, and the aqueous was extracted with ethyl acetate. The combined organic phases were extracted with NaOH and then dried ($Na_2SO_4$), filtered and concentrated (66.8 g of dark brown oil).

56.5 g of this oil were distilled, resulting in 46.3 g of product as a colorless oil.

Example 4

5 3,3-Diphenylbutanoic acid 4.9 g of ethyl 3,3-diphenylbutanoate (18.3 mmol) were dissolved in 30 ml of dioxane, 36 ml of 1M KOH were added, and the mixture was stirred at 60–70° C. for 6 h.

The dioxane was then stripped off in a rotary evaporator, and the aqueous residue was diluted with water and extracted with diethyl ether. The aqueous phase was then adjusted to pH 1 and extracted with ethyl acetate. The organic phase was dried ($Na_2SO_4$), filtered and concentrated. The solid residue was stirred with heptane, resulting in 2.35 g of a white powder (55%). The mother liquor was not purified further.

Example 5

(2R,S)-3,3-Diphenyl-2-(3', 4'-methylenedioxybenzyl)butanoic acid 15 ml of butyllithium (24 mmol, 1.6M in hexane) were added dropwise to a solution of 3,3-diphenylbutanoic acid (2,4 g, 10 mmol) in 40 ml of absolute THF at –20° C., and the mixture was then stirred at from –10 to –20° C. for 1 h. Then piperonyl chloride (2,2 g, 13 mmol) in 10 ml of THF was added, and the mixture was stirred at room temperature for 16 h and then quenched with saturated $NH_4Cl$ solution. The organic phase was separated off, the aqueous phase was extracted with ethyl acetate, and then the combined organic extracts were dried ($Na_2SO_4$), filtered and concentrated. The residue was chromatographed on silica gel ($CH_2Cl_2$/MeOH 19:1), resulting in 2.4 g of the reqired product (65%).

The acid was dissolved in $CH_2Cl_2$ and shaken with saturated sodium carbonate solution. The organic (I) phase was separated off, dried ($Na_2SO_4$), filtered and concentrated. 2.5 g of sodium salt of the acid were obtained.

Melting point: 308–310° C. (decomposition)

Example 6

3,3-Bis(4-methoxy-3-methylphenyl)butanoic acid

Preparation took place as in Example 1b. However, in this case, mainly the corresponding ethyl ester was isolated so that subsequent hydrolysis was necessary (as in Example 4).

Melting point: 121–124° C.

Example 7

(2R,S)-3,3-Bis(4-methoxy-3-methylphenyl)-2-(3', 4'-methylenedioxy-benzyl) butanoic acid Preparation similar to Example 2. 3.25 ml of diisopropylamine (23 mmol), 15.6 ml of butyllithium (23 mmol, 1.5 M in hexane), 3.28 g of 3,3-bis(4-methoxy-3-methylphenyl) butanoic acid (10 mmol), 2.19 g of piperonyl chloride (13 mmol) afford 4.1 g of crude product. Chromatography on silica gel ($CH_2Cl_2$/MeOH 19:1) afforded 1.6 g of product (35%)

Melting point: 152–153° C.

Example 8

(2R,S)-3,3-Diphenyl-2-(3', 4'-dimethoxybenzyl) butanoic acid

Preparation took place as in Example 5. 2.4 g of 3,3-diphenylbutanoic acid (10 mmol), 15.6 ml of butyllithium (23 mmol, 1.5 M in hexane), 2.2 g of 3,4-dimethoxybenzyl chloride (13 mmol) afforded 3.8 g of crude product. Purification on silica gel (heptane/ethyl acetate 1:1) 2.1 g of product (54%)
Melting point: 141–143° C.

Example 9

3,3-Bis(4-methoxyphenyl)pentanoic acid

Ethyl (2E,Z)-3-(4-methoxyphenyl)-2-pentenoate (7.0 g, 30 mmol) was dissolved in anisole (4.9 g, 45 mmol) at 0° C., and 50 ml of 80% $H_2SO_4$ were cautiously added. The 2-phase mixture was vigorously 30 stirred at room temperature for 30 h and then poured onto ice, and the product was extracted with methylene chloride. The organic phase was dried ($Na_2SO_4$), filtered and concentrated, the residue was taken up in ether and extracted with 2 N sodium hydroxide solution, and the ether phase was discarded. The alkaline phase was adjusted to pH 2 with 2N HCl, and the product was extracted with ethyl acetate. The organic phase was then dried ($Na_2SO_4$), filtered and concentrated, and the solid residue was stirred with heptane. The product was filtered off with suction and dried. 6.8 g of a white powder (72%) remained.
Melting point: 136–139° C.

Example 10

(2R,S)-3,3-Bis(4-methoxyphenyl)pentanoic acid 29 ml of butyllithium (46 mmol, 1.6 M in hexane) were added dropwise to a solution of 3,3-bis(4-methoxyphenyl) pentanoic acid (6.2 g, 20 mmol) in 100 ml of absolute THF at −20° C., and the mixture was then stirred at room temperature for 1 h. Then, at −10° C., piperonyl chloride (4.4 g, 24 mmol) in 10 ml of THF was added, and the mixture was stirred at room temperature for 72 h and then quenched with saturated $NH_4Cl$ solution. The organic phase was separated off, the aqueous phase was extracted with ethyl acetate, and then the combined organic extracts were dried ($Na_2SO_4$), filtered and concentrated. The residue (11.2 g) was chromatographed on silica gel ($CH_2Cl_2$/MeOH 24:1), resulting in 3.1 g of the required product (34%).
Melting point: 84–86° C. (stirred in heptane)

Example 11

Methyl 3,3-Bis(4-methoxyphenyl)hexanoate

Anisole (6.6 g, 61 mmol) was dissolved in 200 ml of dichloroethane and, at 0 C, aluminum trichloride (12,3 g, 92 mmol) was added in portions and subsequently, while stirring, methyl (2E,Z)-3-(4-methoxyphenyl)-2-hexenoate (18 g, 61 mmol) was added dropwise. The reaction mixture was stirred at 5° C. for 2 h and then at room temperature for 2 days. For workup, the mixture was poured into ice-water and extracted with $CH_2Cl_2$, and the combined organic phases were washed with saturated NaCl solution and dried over $MgSO_4$. The residue remaining after concentration was purified by chromatography on silica gel (n-heptane/7.5% ethyl acetate). This resulted in 5.2 g (25%) of a colorless oil.
$^1$H-NMR ($CDCl_3$), δ: 0.9 (m, 3H), 1.1 and 2.2 (each m, 2H), 3.08 (s, 2H), 3.4 (s, 3H) (s, 6H), 6.8 and 7.1 (each m, 4H) ppm.

Example 12

3,3-Bis(4-methoxyphenyl)hexanoic acid

Methyl 3,3-bis(4-methoxyphenyl)hexanoate (5.2 g, 15.2 mmol) was introduced into 20 ml of dioxane, KOH (1.05 g, 18.2 mmol) was added, and the mixture was boiled for about 1 h. It was subsequently diluted with water and washed with ethyl acetate, and the aqueous phase was then adjusted to pH 3 with dilute HCl and extracted with ethyl acetate. The organic phase was then washed with saturated NaCl solution, dried over $MgSO_4$ and concentrated. Chromatography on silica gel ($CH_2Cl_2$/methanol 3%) resulted in 4.1 g of a pale yellowish oil (84%).
$^1$H-NMR ($CDCl_3$), δ: 0.9 (m, 3H), 1.1 und 2.2 (each m, 2H), 3.1 (s, 3H), 3.8 (s, 6H), 6.8 and 7.1 (each m, 4H) ppm.

Example 13

The following compounds were prepared as in Example 5.

(2R,S)-3,3-Diphenyl-2-(methyl-2'-naphthyl )butanoic acid Melting point: 163–164° C. FAB-MS: 380 ($M^+$)

(2R,S)-3,3-Diphenyl-2-s(3', 5'-dimethylbenzyl)butanoic acid Melting point: 141–143° C. FAB-MS: 358 ($M^+$)

(2R,S)-3,3-Diphenyl-2- (4'-benzyloxy-3-methoxybenzyl) butanoic acid Melting point: 163–166° C. FAB-MS: 466 ($M^+$)

(2R,S)-3,3-Bis(4- methoxyphenyl)-2-(4-benzyloxy-3-methoxybenzyl )-butanoic acid Melting point: 137–140° C. FAB-MS: 526 ($M^+$)

(2R,S)-3,3-Diphenyl-2-(4'-hydroxy-3'-methoxybenzyl) butanoic acid Melting point: 153–155° C. FAB-MS: 376 ($M^+$)

(2R,S)-3,3-Bis(4-methoxyphenyl)-2-(4'-hydroxy-3-methoxybenzyl)butanoic acid Melting point: 157–160° C. FAB-MS: 436 ($M^+$)

(2R,S)-3,3-Bis(4-methoxy-3-methylphenyl)-2-(3', 5'-dimethyl-benzyl) butanoic acid Melting point: 150–152° C. FAB-MS: 446 ($M^+$)

(2R,S)-3,3-Bis(4-methoxyphenyl )2--2-methyl-21-naphthyl)butanoic acid Melting point: 162–164° C. FAB-MS: 440 ($M^+$)

(2R,S)-3,3-Bis(4-methoxyphenyl)-2-(3', 5'-dimethylbenzyl)butanoic acid Melting point: 125–128° C. FAB-MS: 418 ($M^+$)

(2R,S)-3,3-Bis(4-methoxy-3-methylphenyl)-2-(3', 4'-dimethoxy-benzyl) butanoic acid Melting point: 155–157° C. FAB-MS: 478 ($M^+$)

(2R,S)-3,3-Bis(4-methoxyphenyl)-2-(3', 4'-dimethoxybenzyl)butanoic acid Melting point: 148–150° C. FAB-MS: 450 ($M^+$)

(2R,S)-3,3-Bis(4-methoxyphenyl)-2-(5'-methoxy-3', 4'-methylene-dioxybenzyl) pentanoic acid Melting point: 138–141° C. FAB-MS: 478 ($M^+$)

(2R,S)-3,3-Bis(4-methoxyphenyl)-2-(5-methoxy-3', 4'-methylene-dioxybenzyl) butanoic acid Melting point: 134–136° C. FAB-MS: 464 ($M^+$)

(2R,S)-3,3-Diphenyl-2-(5'-methoxy-3', 4'-methylenedioxybenzyl)-butanoic acid Melting point: 135–138° C. FAB-MS: 464 ($M^+$)

(2R,S)-3,3-Bis(4-methoxyphenyl)-2-(3', 4'-ethylenedioxybenzyl)-pentanoic acid Melting point: 168–170° C. FAB-MS: 462 ($M^+$)

(2R,S)-3,3-Bis(4-methoxyphenyl)-2-(3', 4'-ethylenedioxybenzyl)-butanoic acid Melting point: 161–163° C. FAB-MS: 448 ($M^+$)

(2R,S)-3,3-Bis(4-methoxyphenyl)-2-(3', 4'-methylenedioxybenzyl)-hexanoic acid Melting point: 142–145° C. (from n-heptane)

(2R,S)-3,3-Bis(4-methoxyphenyl)-2-(3', 4'-ethylenedioxybenzyl)-hexanoic acid Melting point: 163–165° C. (from n-heptane/diethyl ether)

(2R,S)-3,3-Bis(4-methoxyphenyl)-2-(3',4'-methylenedioxy-5'-methoxybenzyl) hexanoic acid Melting point: 180–182° C. (from n-heptane/diethyl ether)

Example 14

The compounds prepared in Examples 2 to 10 were checked for their endothelin receptor affinity by the methods described above. A compound disclosed in WO 94/02474 was used as comparison substance. The result is reported in the following Table.

| | $ET_A$ | $ET_B$ |
|---|---|---|
| (WO 94/02474) | 420 nM | >6400 nM |
| (Example 2) | 38 nM | 2800 nM |
| (Example 10) | 6 nM | 1300 nM |

We claim:

1. A carboxylic acid derivative of the formula I

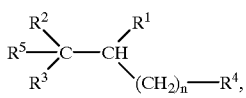

(I)

where $R^1$ is a tetrazolyl radical, a cyanide radical, COOH or a radical which can be hydrolyzed to —COOH and;

$R^2$ and $R^3$, are
phenyl or naphthyl which can be substituted by one or more of the following radicals: halogen, cyano, $NO_2$, hydroxyl, $C_1$–$C_4$-alkyl, $C_1$-$C_4$-haloalkyl, $C_1$–$C_4$-alkoxy, $C_1$–$C_4$-haloalkoxy, phenoxy, $C_1$–$C_4$-alkylthio, amino benzyloxy, $C_1$–$C_4$-alkylamino or $C_1$–$C_4$-dialkylamino; or phenyl or naphthyl which are connected together in the ortho positions by a direct linkage, a methylene, ethylene or ethylene group, or an oxygen or sulfur atom;

$R^4$ is phenyl or naphthyl, methylenedioxyphenyl, ethylenedioxyphenyl, indanyl, indolyl, pyridyl, benzopyranyl, furanyl, pyrimidinyl, benzofuranyl, isooxazolyl, isothiazolyl, 1,3,4-thiadiazolyl, 2,3-dihydrobenzofuranyl, benzothienyl, quinolinyl, $C_3$–$C_7$-cycloalkyl, thienyl, oxazolyl, thiazolyl, each of which are unsubstituted or optionally substituted by one or more of the following radicals: halogen, cyano, hydroxyl, $NO_2$, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino benzyloxy, $C_1$–$C_4$-alkylamino or $C_1$–$C_4$-dialkylamino, it being possible for the alkyl radicals together to form a ring;

$R^5$ is $C_1$–$C_8$-alkyl, $C_3$–$C_6$-alkenyl, $C_3$–$C_6$-alkynyl or $C_3$–$C_8$-cycloalkyl, each of which are unsubstituted or optionally substituted one or more times by: halogen, $C_1$–$C_4$-alkoxy, $C_1$–$C_4$-alkylthio, $C_1$–$C_4$-alkylamino, di-$C_1$–$C_4$-alkylamino; phenyl, benzyl, 1-methylnaphthyl, 2-methylnaphthyl or naphthyl, each of which are unsubstituted or optionally substituted by one or more of the following radicals: halogen, cyano, hydroxyl, amino, $C_1$–$C_4$-alkyl, $C_1$–$C_4$-alkoxy, phenoxy, $C_1$–$C_4$-alkylthio, dioxomethyl or dioxoethyl.

2. A pharmaceutical composition comprising the carboxylic acid derivative defined in claim 1, and a pharmaceutically acceptable carrier.

3. A method of treating hypertension or acute myocardial infaction, which method comprises administering to a mammal an effective amount of the composition defined in claim 2.

* * * * *

UNITED STATES PATENT AND TRADEMARK OFFICE
CERTIFICATE OF CORRECTION

PATENT NO.: 6,004,988

DATED: December 21, 1999

INVENTOR(S): AMBERG et al.

It is certified that error appears in the above-identified patent and that said Letters Patent is hereby corrected as shown below:

In the abstract, line 1 after formula I, "here" should be --where--.

Col. 38, claim 1, line 44, after "dioxoethyl" insert --; n is 1 or 2.--.

Signed and Sealed this

Eighteenth Day of July, 2000

Attest:

Q. TODD DICKINSON

Attesting Officer     Director of Patents and Trademarks